US012763195B2

(12) United States Patent
Shah et al.

(10) Patent No.: US 12,763,195 B2
(45) Date of Patent: Oct. 13, 2026

(54) CONVERSATIONAL ARTIFICIAL INTELLIGENCE SYSTEM WITH MULTI-AGENT ORCHESTRATION AND PARALLEL SUPERVISORY PROCESSING

(71) Applicant: HealthGPT, Inc., Palo Alto, CA (US)

(72) Inventors: Munjal Shah, Palo Alto, CA (US); Vishal Parikh, Palo Alto, CA (US); Meenesh Bhimani, Palo Alto, CA (US); Subhabrata Mukherjee, Palo Alto, CA (US); Alex Miller, Palo Alto, CA (US); Saad Godil, Palo Alto, CA (US); Debajyoti Datta, Palo Alto, CA (US); Paul Gamble, Palo Alto, CA (US); Rae Lasko, Palo Alto, CA (US)

(73) Assignee: HealthGPT, Inc., Palo Alto, CA (US)

( * ) Notice: Subject to any disclaimer, the term of this patent is extended or adjusted under 35 U.S.C. 154(b) by 0 days.

(21) Appl. No.: 19/547,381

(22) Filed: Feb. 23, 2026

(65) Prior Publication Data

US 2026/0188474 A1 Jul. 2, 2026

Related U.S. Application Data

(63) Continuation of application No. 18/900,289, filed on Sep. 27, 2024, which is a continuation of application (Continued)

(51) Int. Cl.

*G10L 15/00* (2013.01)
*G10L 15/183* (2013.01)

(Continued)

(52) U.S. Cl.

CPC ........... *G16H 40/20* (2018.01); *G10L 15/183* (2013.01); *G10L 15/22* (2013.01); *G10L 25/66* (2013.01);

(Continued)

(58) Field of Classification Search

CPC ...... G06F 40/30; G06F 40/211; G06F 40/268; G06F 40/284; G10L 15/16; G10L 19/005;

(Continued)

(56) References Cited

U.S. PATENT DOCUMENTS 7,284,046 B1 10/2007 Kreiner et al.
8,082,349 B1 12/2011 Bhargava et al.

(Continued)

OTHER PUBLICATIONS

Anonymous, Error Handling and Fallback Mechanisms in AI Assistants: A Comprehensive Guide, Nexus Flow Innovations, published on Nov. 11, 2024, 4 pages. Retrieved from the internet on Aug. 8, 2025. URL: https://www.nexusflowinnovations.com/blog/error-handling-fallback-mechanisms-ai-assistants.

(Continued)

*Primary Examiner* — Vu B Hang
(74) *Attorney, Agent, or Firm* — FP; Sikander M. Khan

(57) ABSTRACT

A conversational artificial intelligence system includes a plurality of large language models configured to perform different functions. A routing system routes requests to a large language model best suited for a task associated with the request. A conversation manager coordinates a flow of a conversation between the system and a user using the plurality of large language models. A supervisory module operates in parallel with the conversation to audit responses generated during the conversation and provides feedback that contributes to construction of downstream responses to the user. One or more safety modules prevent the system from performing actions that are outside of defined constraints. The routing system may route requests based on latency requirements, domain, or classification tasks, and may fail over to a different large language model when a first large language model degrades.

20 Claims, 21 Drawing Sheets

Related U.S. Application Data

No. 18/592,441, filed on Feb. 29, 2024, now Pat. No. 12,142,371.

(60) Provisional application No. 63/611,762, filed on Dec. 18, 2023, provisional application No. 63/466,712, filed on May 15, 2023.

(51) Int. Cl.

| | |
|---|---|
| ***G10L 15/22*** | (2006.01) |
| ***G10L 25/66*** | (2013.01) |
| ***G16H 40/20*** | (2018.01) |
| *G10L 15/16* | (2006.01) |
| *G10L 15/18* | (2013.01) |
| *G10L 15/19* | (2013.01) |

(52) U.S. Cl.

CPC .......... *G10L 15/16* (2013.01); *G10L 15/1822* (2013.01); *G10L 15/19* (2013.01)

(58) Field of Classification Search

CPC ......... G10L 19/00; G10L 25/27; G10L 25/30; G10L 15/12; G10L 15/02; G10L 15/063; G10L 15/07; G10L 15/20; G10L 15/22; G10L 15/26; G10L 15/30; G10L 25/78; G10L 25/87; G10L 15/08; G10L 15/1822; G10L 15/183; G10L 15/193; G10L 15/19; G10L 17/18; G10L 15/1815; G10L 13/02

See application file for complete search history.

(56) References Cited

U.S. PATENT DOCUMENTS

| | | | |
|---|---|---|---|
| 8,548,937 | B2 | 10/2013 | Saigal et al. |
| 9,824,188 | B2 | 11/2017 | Brown et al. |
| 10,282,512 | B2 | 5/2019 | Bennett et al. |
| 10,452,816 | B2 | 10/2019 | Kidd et al. |
| 10,504,379 | B2 | 12/2019 | Vinkers et al. |
| 10,748,644 | B2 | 8/2020 | Shriberg et al. |
| 11,329,933 | B1 | 5/2022 | Kiyanda et al. |
| 11,348,694 | B2 | 5/2022 | Kim et al. |
| 11,355,109 | B2 | 6/2022 | Lou et al. |
| 11,438,283 | B1 | 9/2022 | White et al. |
| 11,532,393 | B2 | 12/2022 | Arkoff et al. |
| 11,646,013 | B2 | 5/2023 | Tran et al. |
| 11,693,990 | B1 | 7/2023 | Arkoff et al. |
| 11,694,807 | B2 | 7/2023 | Golan et al. |
| 11,790,894 | B2 | 10/2023 | Mao et al. |
| 11,843,565 | B2 | 12/2023 | Lee et al. |
| 11,977,854 | B2 | 5/2024 | Tunstall-Pedoe et al. |
| 2010/0235899 | A1 | 9/2010 | Li et al. |
| 2014/0365885 | A1 | 12/2014 | Carson et al. |
| 2019/0341052 | A1 | 11/2019 | Allibhai |
| 2020/0137230 | A1 | 4/2020 | Spohrer |
| 2023/0108637 | A1 | 4/2023 | Rabinovich et al. |
| 2023/0245651 | A1 | 8/2023 | Wang |
| 2024/0185968 | A1 | 6/2024 | Doerr et al. |

OTHER PUBLICATIONS

Biao et al, Root Mean Square Layer Normalization, School of Informatics, University of Edinburgh, Retrieved on Jun. 6, 2024, 12 pages. [NeurIPS 2019].

Dosovitskiy et al., An Image Is Worth 16x16 Words: Transformers For Image Recognition At Scale, ICLR 2021, dated Jun. 3, 2021, 22 pages.

Gao et al. Retrieval-Augmented Generation for Large Language Models: A Survey, Shanghai Research Institute for Intelligent Autonomous Systems, Tongji University, Mar. 27, 2024, 21 pages. [Url: arXiv:2312.10997].

Karan et al, Large Language Models Encode Clinical Knowledge, Google Research, Dec. 26, 2022, 44 pages. [arXiv:2212.13138].

McGreevy et al., Clinical, Legal, and Ethical Aspects of Artificial Intelligence-Assisted Conversational Agents in Health Care, JAMA, vol. 324, No. 6, dated Aug. 11, 2020, 2 pages.

Peter et al, Benefits, Limits, and Risks of GPT-4 as an AI Chatbot for Medicine. The New England Journal of Medicine, Mar. 30, 2023, 7 pages [N Engl Med 388;13].

PGR2025-00075—Mandatory Notices, filed on Aug. 25, 2025, 4 pages.

PGR2025-00075—Petition for Post-Grant Review Updated, filed on Aug. 12, 2025, 83 pages.

PGR2025-00075—Petition for Post-Grant Review Updated, filed on Aug. 27, 2025, 4 pages.

PGR2025-00075—Petition for Post-Grant Review Updated, filed on Aug. 27, 2025, 83 pages.

Surani et al., Understanding Privacy and Security Postures of Healthcare Chatbots, CHI-22, Apr. 30-May 6, 2022, 7 pages.

Tao et al., Towards Conversational Diagnostic AI, Google Research, Jan. 11, 2024, 46 pages.

Vaswani et al., Attention Is All You Need, Advances in Neural Information Processing Systems 2017, dated Dec. 6, 2017, 15 pages.

2100

```
batch_size = tf.shape(x)[0]
x = self.rescale(x)
patches = self.extract_patches(x)
x = self.patch_proj(patches)

class_emb = tf.broadcast_to(
    self.class_emb, [batch_size, 1, self.d_model]
)
x = tf.concat([class_emb, x], axis=1)
x = x + self.pos_emb

for layer in self.enc_layers:
    x = layer(x, training)

return  self.mlp_head(x[:, 0])
```

FIG. 21

CONVERSATIONAL ARTIFICIAL INTELLIGENCE SYSTEM WITH MULTI-AGENT ORCHESTRATION AND PARALLEL SUPERVISORY PROCESSING

PRIORITY DATA

This application is a continuation of U.S. patent application Ser. No. 18/900,289, filed Sep. 27, 2024, which is a continuation of U.S. patent application Ser. No. 18/592,441, filed Feb. 29, 2024, now U.S. Pat. No. 12,142,371, which claims the benefit of U.S. Provisional Patent Application No. 63/611,762, filed Dec. 18, 2023, and U.S. Provisional Patent Application No. 63/466,712, filed May 15, 2023. Each of the foregoing applications is incorporated herein by reference in its entirety and for all purposes.

BACKGROUND OF THE TECHNOLOGY DISCLOSED

Field of the Technology Disclosed

The technology disclosed relates to artificial intelligence type computers and digital data processing systems and corresponding data processing methods and products for emulation of intelligence (i.e., knowledge based systems, reasoning systems, and knowledge acquisition systems); and including systems for reasoning with uncertainty (e.g., fuzzy logic systems), adaptive systems, machine learning systems, and artificial neural networks. In particular, the technology disclosed relates generally to systems and techniques to provide a low-latency conversational artificial intelligence (AI) architecture with a parallelized in-depth analysis feedback loop for healthcare-related applications.

DESCRIPTION OF THE RELATED ART

Current AI virtual assistants (which include chat bots), such as ChatGPT and the like, are not designed for use in healthcare fields and so have a variety of issues. For example, current AI virtual assistants are incapable of following a checklist, are too verbose for multi-turn conversations, are not designed to engage with humans, and are not designed to comply with medical safety laws, regulations, and procedures.

SUMMARY OF THE TECHNOLOGY DISCLOSED

This Summary provides a simplified form of concepts that are further described below in the Detailed Description. This Summary is not intended to identify key or essential features and should therefore not be used for determining or limiting the scope of the claimed subject matter.

In some aspects, an artificial intelligence that is configured to complete a checklist during a conversation initiates the conversation with a human. The artificial intelligence receives a first human response from the human, extracts data from the first human response, and stores the data in a conversation summary. The artificial intelligence provides a first artificial intelligence response to the human. The artificial intelligence receives a second human response from the human, accesses the conversation summary, and provides a second artificial intelligence response to the human based at least in part on a portion of the data in the conversation summary. The artificial intelligence, based at least in part on determining that the checklist has been completed, ends the conversation with the human.

BRIEF DESCRIPTION OF THE DRAWINGS

A more complete understanding of the present disclosure may be obtained by reference to the following Detailed Description when taken in conjunction with the accompanying Drawings. In the figures, the left-most digit(s) of a reference number identifies the figure in which the reference number first appears. The same reference numbers in different figures indicate similar or identical items.

FIG. 21 shows example software code that implements a Transformer block.

DETAILED DESCRIPTION

Figure 1:
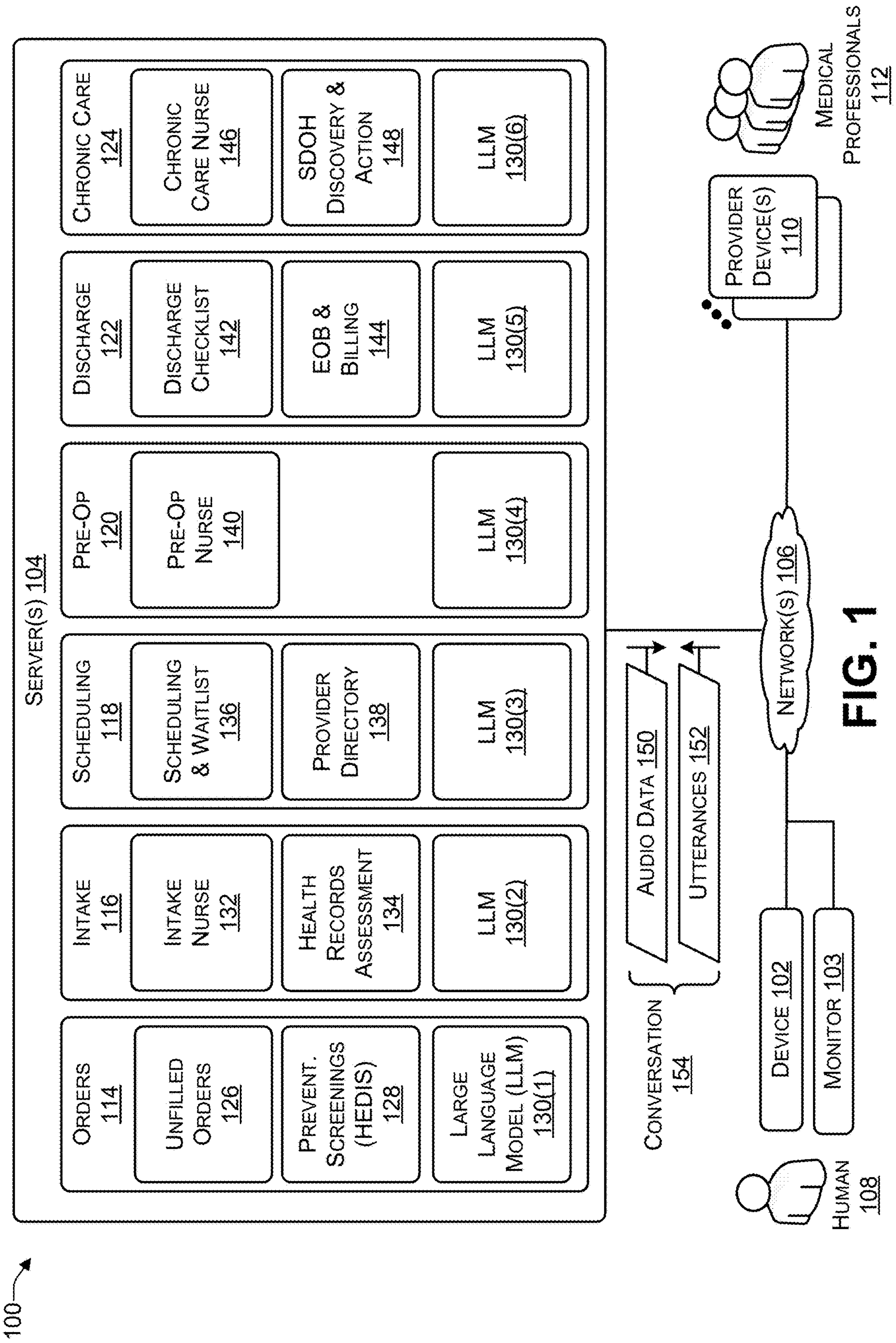
FIG. 1 is a block diagram of a system illustrating large language models (LLMs) to perform specialized healthcare-related functions, according to some implementations.

The technology disclosed can be practiced as a system, method, or article of manufacture. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

One or more implementations and clauses of the technology disclosed, or elements thereof can be implemented in the form of a computer product, including a non-transitory computer readable storage medium with computer usable program code for performing the method steps indicated. Furthermore, one or more implementations and clauses of the technology disclosed, or elements thereof can be implemented in the form of an apparatus including a memory and at least one processor that is coupled to the memory and operative to perform exemplary method steps. Yet further, in another aspect, one or more implementations and clauses of the technology disclosed or elements thereof can be implemented in the form of means for carrying out one or more of the method steps described herein; the means can include (i) hardware module(s), (ii) software module(s) executing on one or more hardware processors, or (iii) a combination of hardware and software modules; any of (i)-(iii) implement the specific techniques set forth herein, and the software modules are stored in a computer readable storage medium (or multiple such media).

The clauses described in this section can be combined as features. In the interest of conciseness, the combinations of features are not individually enumerated and are not repeated with each base set of features. The reader will understand how features identified in the clauses described in this section can readily be combined with sets of base features identified as implementations in other sections of this application. These clauses are not meant to be mutually exclusive, exhaustive, or restrictive; and the technology disclosed is not limited to these clauses but rather encompasses all possible combinations, modifications, and variations within the scope of the claimed technology and its equivalents.

Other implementations of the clauses described in this section can include a non-transitory computer readable storage medium storing instructions executable by a processor to perform any of the clauses described in this section. Yet another implementation of the clauses described in this section can include a system including memory and one or more processors operable to execute instructions, stored in the memory, to perform any of the clauses described in this section.

The systems and techniques described herein provide an artificial intelligence (AI) based virtual assistant, which may use a large language model (LLM), for use in healthcare. For example, the AI based virtual assistant may be implemented as a virtual assistant to perform tasks that are normally performed by medical professionals (e.g., nurses, medical assistants, care coordinators, etc.). The AI-based virtual assistants invented herein are (i) capable of following a checklist (e.g., they do not get distracted while engaging in a conversation with a human), (ii) designed to engage in multi-turn conversations with humans, (iii) designed to comply with medical safety laws, regulations, and procedures, and (iv) show a consistent level of empathy towards the human. For example, the AI-based virtual assistant may engage in tasks such as preventative screenings, performing intake-related tasks, performing scheduling and waitlisting, pre-op related tasks, discharge-related tasks (including explanation of benefits (EOB) and billing), and chronic care related tasks (e.g., periodic follow ups). In this way, when the AI-based virtual assistant are used, staff shortages can be ameliorated, costs reduced, and human medical staff can be refocused on in-person tasks. An LLM is used herein as an example of an AI to implement the systems and techniques. It should be understood that other types of AI may be used along with or in place of an LLM.

The systems and techniques described herein provide several advantages over conventional virtual assistants, including commercially available LLM based chatbots. First, the systems and techniques enable an AI-based virtual assistant to engage in long conversations (e.g., 50 or more turns) with a human. The term "turn" is used in reference to a multi-party interaction, and means each piece of content communicated by one party between communications by other parties. For example: Person 1: "Hello" (turn 1), Person 2: "Hi, how are you? (turn 2), 3. Person 1: "I'm doing well, how about you?" (turn 3), Person 2: "Also good. This is my friend." (turn 4), Person 3 "Nice to meet you." (turn 5), etc. Traditional virtual assistant interactions typically involve fewer than four turns, and thus do poorly on tasks that involve greater interaction with memory of earlier parts of a conversation. The systems and techniques described herein allow for a virtual assistant to engage in longer, multi-turn conversations. The AI-based virtual assistant described herein can also complete a checklist; a task that conventional virtual assistants struggle with. For example, the AI-based virtual assistant may be trained using multi-turn reinforcement learning through human feedback (RLHF) or other similar techniques. Multi-turn reinforcement learning through human feedback involves assessing the output of the LLM over an entire conversation (or multiple turns) rather than conventional methods which assess each question-answer pair. The AI-based virtual assistant may be trained to identify turn-yielding cues, interruption detection, and identifying non-verbal cues. For example, if the human coughs, sneezes, starts crying, or the like, the AI-based virtual assistant asks follow-up questions, such as "How long have you had that cough/congestion?" and the like. The AI-based virtual assistant may also be trained to exhibit a desired level of empathy towards the human. For example, certain humans may respond better to a more direct conversational tone, while others may respond better to more supportive conversational styles. The virtual assistant's level of empathy may be implemented using multi-turn reinforcement learning with human feedback. The desired level of empathy may be dynamic, based on information known about the human. Such information may be derived from previous conversations between the AI-based virtual assistant and the human, or other profile information of the human. Such personalization may lead to better outcomes for the human, such as better compliance with prescriptions, more sustained lifestyle changes, etc., and also create an effective health coach. The AI-based virtual assistant may also be used to collect longitudinal health information to track and respond to patient progress over time.

Second, the systems and techniques are designed to reduce the latency of the AI-based virtual assistant's output during a conversation with a human. The AI-based virtual assistant may perform predictive answering by continuously generating multiple possible responses and then accepting/discarding responses based on receiving an additional human response from the human, thereby reducing latency. During the conversation, the systems and techniques may extract facts from the conversation (e.g., based on information provided by the human) and construct a knowledge graph that can be accessed by the AI-based virtual assistant during the conversation. In this way, if the human mentions something related to a much earlier human utterance, the AI-based virtual assistant is able to quickly determine what the human is referring to, thereby reducing latency (compared to searching through the entire conversation up to that point in time). The purpose of reducing latency is to prevent the human from ending the conversation in frustration or due to the human erroneously concluding that the conversation has concluded or the virtual assistant has encountered an error.

Third, the systems and techniques provide for a retro-generative conversational system in which, while the conversation between the AI-based virtual assistant and the human is taking place, a second AI performs an in-depth analysis, thereby creating a low-latency conversational artificial intelligence (AI) architecture with a parallelized in-depth analysis feedback loop. If the second AI determines that a previous response provided by the AI-based virtual assistant could be clarified (or expanded upon), the second AI provides information regarding the clarification (or expansion), and the AI-based virtual assistant provides the clarification (or expansion) in the conversation. In this way, the human does not notice any latency because the in-depth analysis performed by the second AI is performed in parallel, e.g., while the AI-based virtual assistant is engaged in a conversation with the human.

Fourth, the systems and techniques provide for a set of kickout conditions. When the AI-based virtual assistant determines that a particular kickout condition has occurred, it transfers the conversation to a medical professional (human being). For example, if the human indicates that they are experiencing a particular symptom that requires more immediate medical attention, then the conversation is transferred to a medical professional (human), such as a nurse. To illustrate, if the human mentions that they are experiencing pain in a particular area of their body (e.g., chest pains, abdominal pains, or the like), then the AI-based virtual assistant may transfer the conversation to a medical professional. In addition, the AI-based virtual assistant may provide the medical professional with a text-based summary, including why the conversation was initiated and what information the human had provided up to that point in time. For example, the AI-based virtual assistant may indicate that the human underwent a medical procedure (e.g., surgery) on a particular date, the conversation was initiated as a post-operative follow-up, and the human indicated during the conversation that they are experiencing particular symptoms (e.g., shortness of breath, rapid heartbeat, dizziness, or the like).

As a first example, a multi-turn conversational system, includes a first large language model-based conversation interface configured to execute multiple turns of human-like conversation with a user. The first large language model-based conversation interface is trained with over one thousand gradient update iterations. The multi-turn conversational system includes a control logic that is in communication with the first large language model-based conversation interface and is configured to generate one or more control signals based on evaluating multiple turns of upstream human-like conversation between the first large language model-based conversation interface and the user. The control signals contribute in part to the construction of multiple turns of downstream human-like conversation between the first large language model-based conversation interface and the user. The control logic may include a trigger detection logic, a question insertion logic, and an answer classification logic. The trigger detection logic may include a second large language model. The answer classification logic may include a third large language model. The trigger detection logic may be configured to evaluate the multiple turns of upstream human-like conversation and to detect trigger exchanges in the multiple turns of upstream human-like conversation that require invoking the question insertion logic. The question insertion logic may be configured to select one or more questions that correspond to the detected trigger exchanges and to cause the first large language model-based conversation interface to use the selected questions to construct the multiple turns of downstream human-like conversation. For example, the selected questions may include the control signals. The first large language model-based conversation interface may be further configured (i) to pose to the user the selected questions, (ii) to receive from the user answers to the selected questions, and (iii) to transmit the received answers to the answer classification logic. The answer classification logic may be configured (i) to analyze the received answers and classify the received answers to at least one answer category in a plurality of answer categories and (ii) to generate the control signals based on the classification. The control signals, generated in response to the answer classification logic classifying the received answers to a first kickout category, may cause the first large language model-based conversation interface to end the human-like conversation with the user. The first large language model-based conversation interface emulates a human healthcare professional. The user is a human being. The human-like conversation is a healthcare-related conversation. The trigger exchanges include symptom descriptors that identify one or more symptoms. The selected questions may include medical condition queries that probe at least one symptom mentioned by the human and identified by at least one symptom descriptor associated with the detected trigger exchanges. The received answers may identify one or more medical conditions associated with the symptom and experienced by the human. The answer classification logic may be further configured to classify the received answers and generate the control signals based on severity of the identified medical conditions. The control signals, generated in response to the answer classification logic classifying the received answers to a second kickout category, may cause the first large language model-based conversation interface to connect the user with a human healthcare professional. The control signals, generated in response to the answer classification logic classifying the received answers to a third kickout category, may cause the first large language model-based conversation interface to schedule a healthcare appointment of the user with a human healthcare professional. The human-like conversation may be text-based, audio-based, or a combination of both.

As a second example, a multi-turn conversational system includes: (i) a conversation interface configured to execute multiple turns of human-like conversation with a user and (ii) a control logic, in communication with the conversation interface, and configured to generate one or more control signals based on evaluating multiple turns of upstream human-like conversation between the conversation interface and the user. In some cases, the control signals may contribute in part to construction of multiple turns of downstream human-like conversation between the conversation interface and the user.

As a third example, a retro-improving conversational system includes a large language model-based conversation interface configured to execute multiple turns of human-like conversation with a user. At least some of the multiple turns include a human-machine response pair. The human-machine response pair includes a human response by the user and a machine response by the large language model-based conversation interface to the human response. The large language model-based conversation interface is trained with over one thousand gradient update iterations. The retro-improving conversational system includes a retro-improvement logic that is in communication with the large language model-based conversation interface and is configured to detect that at least one previously expressed human-machine response pair requires an improvement. The previously expressed human-machine response pair includes a previously expressed human response by the user and a previously expressed machine response by the large language model-based conversation interface to the previously expressed human response. The retro-improvement logic is further configured to generate an improved machine response that improves the previously expressed machine response and to cause expression of the improved machine response to the user. The retro-improvement logic may be further configured to analyze the previously expressed human-machine response pair and, based on the analysis, select from a plurality of specialist engines, at least one specialist engine that is specific to the previously expressed human-machine response pair. The selected specialist engine may be configured to generate the improved machine response in response to processing the previously expressed human-machine response pair. The improved machine response may correct the previously expressed machine response. The previously expressed machine response may be supplemented by the improved machine response. The improved machine response may be concurrently presented with the previously expressed machine response. The large language model-based conversation interface may be a multi-head attention model. The respective specialist engines in the plurality of specialist engines may be respective large language models. The specialist engines may have different model parameter footprints than the large language model based conversation interface. The model parameter footprints of the specialist engines may be smaller than a model parameter footprint of the large language model-based conversation interface. The respective specialist engines may be configured to execute respective follow-on tasks in response to processing the previously expressed human-machine response pair. The improved machine response may be preceded by one or more intermediate human-machine response pairs being exchanged between the large language model-based conversation interface and the user. The improved machine response immediately may succeed the previously expressed machine response. The large language model-based conversation interface may emulate a human healthcare professional, the user may be a human being, and the human-like conversation may be a healthcare-related conversation. The plurality of specialist engines may include a kickout to human healthcare professional engine, a dosage engine, a co-morbidity engine, a family history engine, or any combination thereof. The kickout to human healthcare professional engine's follow-on task may immediately transfer the human-like conversation to a human nurse and the dosage engine's follow-on task may include to seek a review of the human's medication by a human nurse and schedule a dosage review call. The human-like conversation may be text-based, audio-based, or a combination of both.

As a fourth example, a retro-improving conversational system may include a conversation interface configured to execute multiple turns of human-like conversation with a user. At least some of the multiple turns include a human-machine response pair. The human-machine response pair includes a human response by the user and a machine response by the conversation interface to the human response. The retro-improving conversational system may include a retro-improvement logic that is in communication with the conversation interface and is configured to detect that at least one previously expressed human-machine response pair requires an improvement. The previously expressed human-machine response pair includes a previously expressed human response by the user and a previously expressed machine response by the conversation interface to the previously expressed human response. The retro-improvement logic is further configured (1) to generate an improved machine response that improves the previously expressed machine response and (2) to cause expression of the improved machine response to the user. In some cases, the conversation interface may be a large language model.

FIG. 1 is a block diagram of a system 100 illustrating large language models (LLMs) to perform specialized healthcare-related functions (e.g., roles), according to some implementations. The system 100 includes a device 102 connected to one or more servers 104 via one or more networks 106. The device 102 may be, for example, a smart phone, or another type of user device associated with a human 108. For example, the human 108 may be a current patient, a past patient, or a potential (future) patient. In some cases, the device 102 may be linked ("paired") with a monitoring device ("monitor") 103, such as a smart watch, a continuous glucose monitor (CGM), or another type of device that is capable of providing biometric readings associated with the human 108 to the device 102.

One or more provider devices 110 may be connected to the network 106. The provider devices 110 may be used by one or more medical professionals 112 (e.g., medical technicians, nurses, nurse practitioners, doctors, and the like) associated with a medical provider.

The server 104 may host multiple AI-based virtual assistants, such as the large language model (LLM) 130 virtual assistants. The virtual assistants LLM 130(1) to 130(6) shown in FIG. 1 each perform a particular healthcare-related role. Six LLM 130 are shown purely for illustration purposes. It should be understood that the number of virtual assistants LLM 130 may vary depending on how the healthcare functions (roles) are divided. The division of the healthcare functions influences the algorithm design, training data, and other details associated with the virtual assistants 130. A different division of the healthcare functions may result in fewer or more than six virtual assistants LLM 130. For illustration purposes, the six functions (roles) include orders 114, intake 116, scheduling 118, pre-op 120, discharge 122, and chronic care 124.

The orders 114 role may include the LLM 130(1) engaging in a conversation 154 with the human 108 to resolve unfilled orders 126. Unfilled orders 126 refers to prescribed medications that the human 108 has not picked up, prescribed medical procedures or follow-up appointments that the human 108 has not scheduled, and so on. The orders 114 role may include the LLM 130(1) entering into a conversation 154 with the human 108 to perform preventative screenings 128, including gathering data relative to Healthcare Effectiveness Data and Information Set (HEDIS) calculations.

The conversation 154 may include audio data 150 output by one of the LLM 130 and one or more utterances 152 from the human 108. The human 108 may speak the utterances 152 into a microphone of the device 102 and the device 102 may send the utterances 152 to the LLM 130 over the network 106. The LLM 130 may provide audio data 150 over the network 106 for playback by the device 102 to the human 108. The conversation 154 may be initiated by the LLM 130 or by the human 108.

The intake 116 role may include the LLM 130(2) engaging in the conversation 154 to perform the role of an intake nurse 132. For example, the conversation 154 may include the LLM 130(2) providing the human 108 with appointment-related information, such as a location and date and time associated with the appointment. The intake 116 role may include the LLM 130(2) engaging in the conversation 154 to perform a Health Records Assessment (HRA), determine a Risk Adjustment Factor (RAF), or the like.

The scheduling 118 role may include the LLM 130(3) engaging in the conversation 154 with the human 108 to perform scheduling and waitlisting related actions. For example, the LLM 130(3) may schedule the human 108 for an appointment and/or waitlist the human 108 for a consultation, surgery, or another type of appointment. The scheduling 118 role may include the LLM 130(3) engaging in the conversation 154 with the human 108 to access a provider directory to select a provider for the human 108. For example, if the human 108 has been asked (e.g., by a primary care physician) to have a consultation with a specialist, then the LLM 130(3) may identify a particular specialist in the provider directory 138 and schedule the human 1084 consultation with the particular specialist.

The pre-op 120 role may include the LLM 130(4) engaging in the conversation 154 and taking on the role of a pre-op nurse 140 to go through a pre-op checklist with the human 108. For example, the pre-op checklist may include various pre-op do's and don'ts, such as what to eat, what not to eat (e.g., avoid solid foods at least 24 hours prior to a colonoscopy, avoid eating 12 hours prior to a blood glucose test, etc.), what medications to take, what medications to avoid taking (e.g., no beta blockers prior to a treadmill stress test), type of clothing to wear (e.g., loose clothing prior to a treadmill stress test), and so on.

The discharge 122 role may include the LLM 130(5) engaging in the conversation 154 to go over a discharge checklist 142. For example, the discharge checklist 142 may include describing what to do and what not do (e.g., don't perform certain action for a particular period of time after certain types of surgery), reviewing medications to take (e.g., take X every day, take Y as needed, and the like), highlighting warning signs (e.g., call medical provider immediately if the human 108 experiences particular symptoms, such as shortness of breath, dizziness, blurry vision, or the like), making follow-up appointments, and the like. The discharge 122 role may include the LLM 130(5) providing information regarding insurance coverage, explanation of benefits (EOB), and other billing-related information (e.g., amount that insurance should cover, amount that the human is responsible for paying, and so on).

The chronic care 124 role may include the LLM 130(6) performing the role of a chronic care nurse when engaging in the conversation 154 with the human 108. For example, the chronic care 124 role may include reviewing medical records and test results, and providing information regarding self-management, such as direct/nutrition suggestions, exercise suggestions, advice on managing prescription regimens, and information regarding monitoring symptoms. The chronic care 124 role may include the LLM 130(6) engaging in the conversation 154 to determine social determinants of health (SDOH), which are the non-medical factors that influence health outcomes. SDOH include the conditions in which people are born, grow, work, live, and age, and the systems shaping the conditions of daily life, such as economic policies, development agendas, social norms, social policies, and political systems.

Thus, a medical provider may deploy AI engines, in the form of a large language model (LLM) or similar AI, to perform specialized health-related tasks. Each AI engine may be designed and trained for a particular purpose, such as screening, intake, scheduling, pre-op, discharge, chronic care, and the like. The advantages of using AI engines include (i) reducing costs compared to using a human, (ii) freeing up humans to perform in-person functions (roles), (iii) performing the health-related tasks at times that are convenient, including outside regular business hours, and (iv) reducing human error when performing the health-related tasks.

Figure 2:
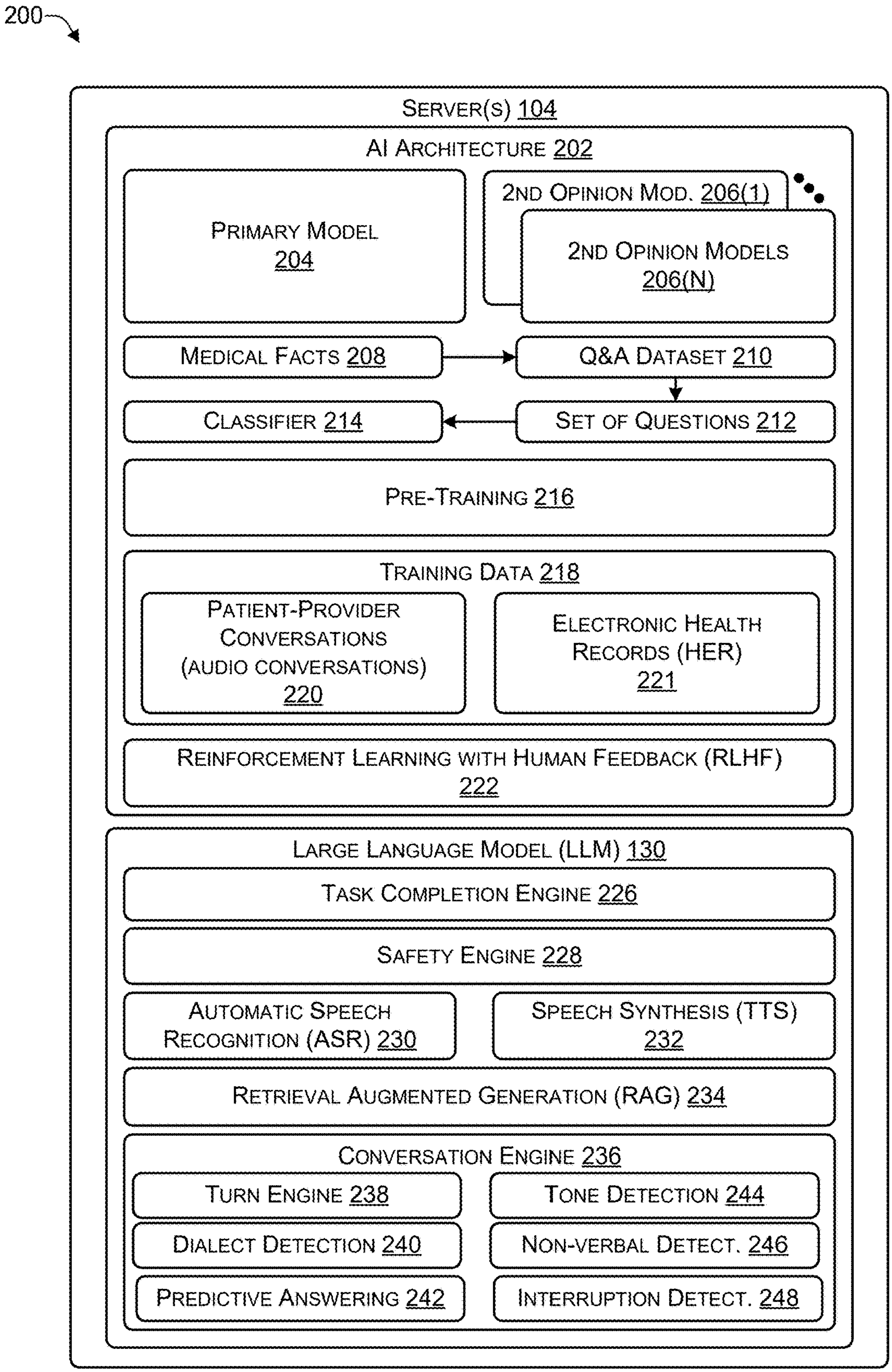
FIG. 2 is a block diagram illustrating an artificial intelligence (AI) architecture, according to some implementations.

FIG. 2 is a block diagram 200 illustrating an artificial intelligence (AI) architecture 202, according to some implementations. The AI architecture 202 may be used to implement one or more of the LLMs (e.g., LLM 130(1), 130(2), 130(3), 130(4), 130(5), and 130(6) of FIG. 1) described herein.

The AI architecture 202 may include a primary model 204 which implements a primary role, such as screening, intake, scheduling, pre-op, discharge, chronic care, or any combination thereof. One or more second opinion models 206(1) to 206(N) (N>0) may be associated with the primary model 204. The second opinion models 206 are AI models, such as LLMs, that are trained to perform a more in-depth analysis than the LLM 130. Based on information extracted from the conversation 154 (of FIG. 1), one of the second opinion models 206 may perform a detailed (e.g., lengthy) analysis while the human 108 is engaged in the conversation 154 with one of the LLM 130. For example, the primary model 204 may have a 50 millisecond (ms) latency while the individual second opinion models 206 may have a 200 ms latency. If the second opinion model 206 determines that particular information provided by the LLM 130 during the conversation 154 can be clarified or expanded upon, then the second opinion model 206 may provide, to the LLM 130, the particular information along with a suggestion regarding how to present the particular information to the human 108. In this way, the primary model tool for and the second opinion models 206 are part of a low-latency conversational artificial intelligence (AI) architecture with a parallelized in-depth analysis feedback loop for healthcare-related applications. The purpose of reducing latency is to prevent the human from hanging up in frustration or due to the human erroneously concluding that the conversation has concluded or the virtual assistant has encountered an error.

A large corpus of medical facts 208 are gathered and converted into a Question & Answer (Q&A) dataset 210. The Q&A dataset 210 may be used to create a set of questions 212. For example, the medical facts 208, such as a description of an illness from a textbook, and converting the description into a Q&A structure, including "What is <illness>?", "What are the symptoms of <illness>?", "How is <illness> treated?", "Who usually gets <illness>?", "Is <illness> common?", and so on. Similarly, tables and other structured data included in the medical facts 208 are converted into a Q&A structure. One or more additional LLMs may be used to determine whether a particular question in the set of questions 212 is relevant. A classifier 214 (e.g., a support vector machine (SVM) or another type of classifier) is used to determine (predict) a distance between individual questions and their corresponding answer to determine if the answer is correct. In pre-training 216, a question is a prompt (e.g., a query presented to the models 204, 206) and the answer is the response predicted by the models 204, 206. The Q&A dataset 210 may be used to fine tune the LLM 130. For example, instruction tuning may be used to further train the LLM 130 on the Q&A dataset 210 (e.g., that is in the form of (instruction, output) pairs), in a supervised fashion.

Training data 218 includes human-provider (e.g., patient-medical professional) conversations 220 in the form of audio data and electronic healthcare records (EHR) 221. By training the LLM 130 using conversation data, the LLM 130 is more suited to engaging in the conversation 154 with the human 108. The AI architecture 202 includes providing the LLM 130 with reinforcement learning with human feedback (RLHF) in which the LLM 130 is trained using a reward function ("reward model") based on human feedback. The reward function provides the LLM 130 with a high reward for good output and a low reward for bad (poor) output. In this way, the LLM 130 is trained to provide the appropriate at each turn in a conversation.

The LLM 130 (representing one of the LLMs 130(1) to 130(6) of FIG. 1) includes a task completion engine 226 that is tasked with completing a checklist during a particular conversation with the human. The task completion engine 226 enables the LLM 130 to complete tasks included in the checklist even while pursuing peripheral matters during the conversation, where such peripheral matters may help to build rapport between the virtual assistant and the human. For example, during the conversation with the human, the human may ask a question, such as a request for clarification of a particular topic ("Can I eat X prior to having the procedure?"). In response, the LLM 130 may provide information to answer the human's question. The LLM may also engage in banter about favorite foods, or the human's experiences with the foods, etc. After the LLM 130 answers the human's question and or engages in banter, the task completion engine 226 causes the LLM 130 to resume addressing items in the checklist. The LLM 130 may include a safety engine 228 to determine a medical accuracy of the information provided by the LLM 130 to the human. The safety engine 228 may determine when to perform a "kick out" and transfer a conversation between a human and an LLM to a medical professional.

The LLM 130 includes an automatic speech recognition module (ASR) 230 to perform speech recognition of the utterances 152 provided by the human 108. The LLM 130 includes a speech synthesis module 232 to perform text-to-speech (TTS) conversion. For example, after the LLM 130 looks up text-based information, the information is provided to the human in the form of speech using the speech synthesis module 232.

The LLM 130 includes a retrieval augmented generation (RAG) module 234. The RAG 234 is an AI framework to retrieve facts from an external knowledge base to provide the LLM 130 accurate and up-to-date information. The RAG 234 grounds the LLM 130 on external sources of knowledge to supplement the LLM 130. Implementing RAG 234 in an LLM-based question answering system enables the LLM 130 to access current, reliable facts, and the access to the sources of the LLM 130, enables output of the LLM 130 to be checked for accuracy. Using RAG, the AI-based virtual assistant described herein can provide accurate answers to a large number of questions that a human could not, such as menu options for a large number of local restaurants, details for a large number of insurance policies, details about a large number of hospital facilities (such as parking information, department locations, etc.).

The LLM 130 includes the conversation engine 236. The conversation engine 236 includes a turn engine 238, dialect detection 240, predictive answering 242, tone detection 244, nonverbal detection 246, and interruption detection 248. The turn engine 238 determines when the human has completed a turn and the LLM 130 has a turn in the conversation. The dialect detection 240 detects a dialect in the utterances of the human and causes the LLM 130 to output audio data having the same (or similar) dialect. For example, the dialect detection 240 may detect the dialect based on a particular word or a particular phrase in the human's utterances. To illustrate, the particular word or the particular phrase may be a vernacular term used in a particular geographic region.

The predictive answering 242 may predict multiple responses that the human may utter based on what the LLM 130 previously provided to the human. For example, the LLM 130 may provide a particular output (audio data) during the LLM's turn and then listen to the human during the human's turn. The predictive answering 242 may predict (i) possible human responses and (ii) corresponding answers based at least in part on the particular output provided during the LLM's turn. After the human has completed providing utterances in the human's turn, the LLM 130 may determine which of the predicted human responses the human provided and select a corresponding predicted answer. In this way, the predictive answering 242 is able to reduce the latency when providing a response after the human's turn.

The tone detection 244 is able to detect that the tone and changes to the tone in the human's utterances during the conversation. For example, the tone detection 244 may be able to detect a tone of the human's utterances, correlate the tone with a particular mood, and adjust the audio data output by the LLM 130 accordingly. To illustrate, the tone of the human's utterances may be determined based on a pitch of the utterances, a volume of the utterances, a particular word in the utterances, a particular phrase in the utterances, or any combination thereof. If a particular tone is detected, such as that of anger or frustration, then the LLM 130 may adjust the audio data output accordingly, including changing the pitch of the audio data, changing a volume of the audio data, inserting a particular word or a particular phrase in the audio data, or any combination thereof. In some cases, if the tone of the human is regressing instead of progressing (e.g., the human has become more angry or more frustrated in a subsequent turn), then the LLM 130 may offer to transfer ("kick out") the conversation to a human. The non-verbal detection 246 may detect the human coughing, sneezing, sighing, crying, or providing another nonverbal audio cue. Detecting one of the nonverbal audio cues may cause the LLM 130 ask additional (e.g., follow-up) questions, such as "How long have you had that cough?" (in response to detecting a cough), "How long have you had nasal congestion?" (in response to detecting a sneeze or sniffling), "Are you feeling okay?" (in response to detecting a loud sigh or crying), or the like. The interruption detection 248 may detect when the human is attempting to interrupt the LLM 130 and cause the LLM 132 yield its turn and provide the human with a turn to enable the human to interject additional utterances into the conversation.

Thus, an AI architecture may include a primary model and one or more second opinion models to provide a low-latency conversational AI with a parallelized in-depth analysis and feedback loop in which the primary model engages in a low latency conversation with the human while the second opinion model gathers additional data and provides feedback (e.g., clarification or expansion of something that the primary model said to the human). Unlike conventional conversational AI's, the training data includes human provider audio-based conversations in addition to text-based training data. The LLM is trained using RLHF to provide improved conversational abilities to the LLM. The LLM may use a task completion engine to avoid missing any items on a checklist of items to be covered with the human. The conversation engine used by the LLM may include a turn engine to determine when the human's turn has ended and the LLM's turn begins, dialect detection to understand and respond to the human in a local dialect, predictive answering to reduce latency by predicting possible answers while the human is talking, tone detection to detect emotional cues (e.g., based on a change in pitch, a change in volume, or the like) in the human's voice, non-verbal detection (e.g., coughing, sneezing, crying, or the like), and interruption detection to detect when the human is attempting to interrupt the LLM. In this way, the LLM is able to provide an engage in a conversation with a human in a manner similar to a human. The purpose of reducing latency is to prevent the human from hanging up in frustration or due to the human erroneously concluding that the conversation has concluded or the virtual assistant has encountered an error.

Figure 3:
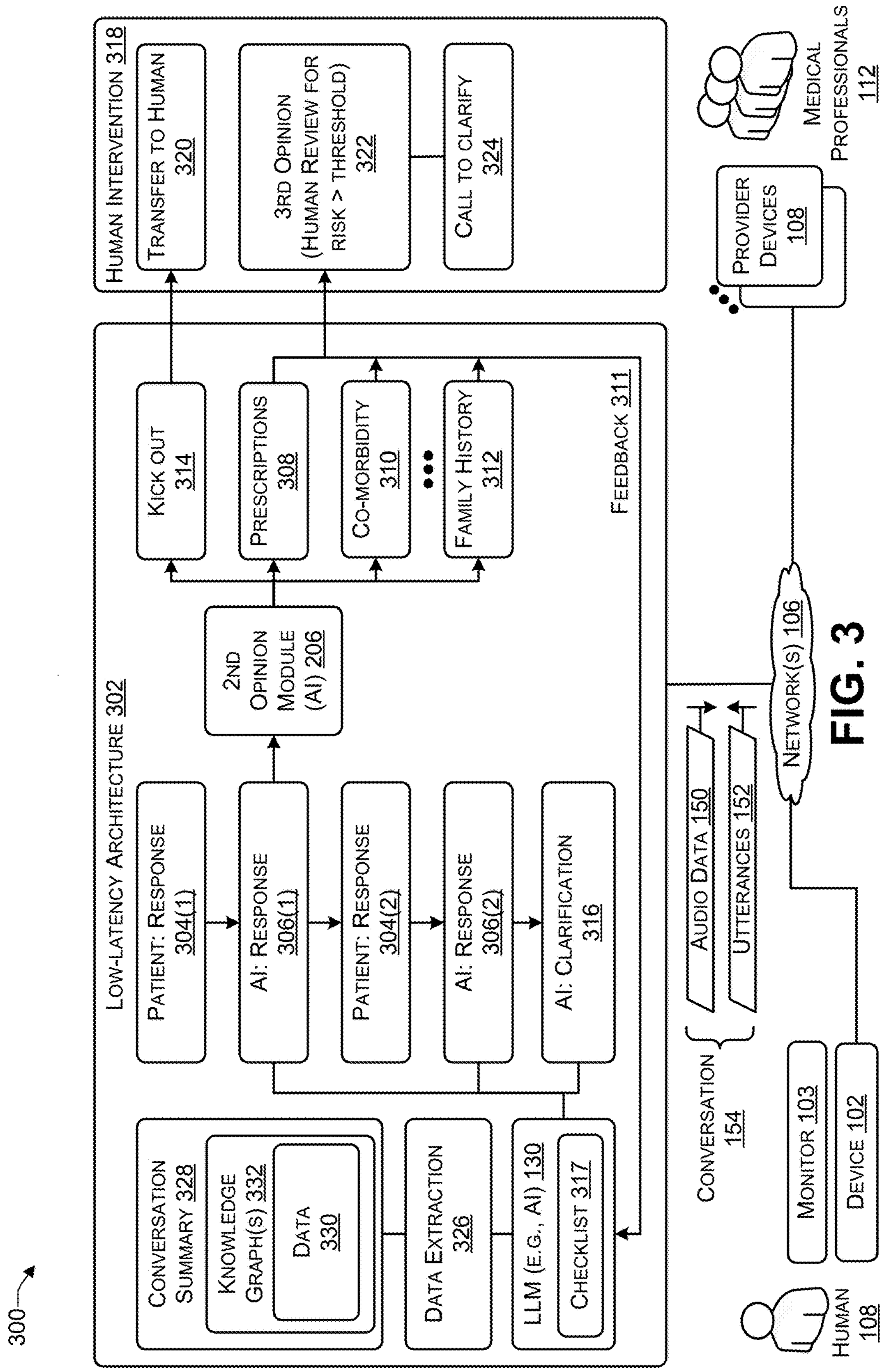
FIG. 3 is a block diagram of a system that includes a low-latency conversational artificial intelligence (AI) architecture with a parallelized in-depth analysis and feedback loop, according to some implementations.

FIG. 3 is a block diagram of a system 300 that includes a low-latency conversational artificial intelligence (AI) architecture with a parallelized in-depth analysis and feedback loop, according to some implementations. The system 300 includes a low latency architecture 302 in which the LLM 130 receives a (first) response 304(1) from the human 108. The LLM 130 may engage in the conversation 154 with the human 108 based on a checklist 317 that identifies tasks that the LLM 130 is to complete during the conversation 154. The LLM 130 provides a (first) response 306(1) to the human 108. The LLM 130 receives a (second) response 304(2) from the human 108 and provides a (second) response 306(2) to the human 108. While the LLM 130 is engaged in the conversation 154 with the human 108, the second opinion module 206 may, in parallel (substantially at the same time), do a lengthier "deep dive" by performing research into the human response 304(1) and the AI response 306(1). For example, the research may include prescriptions 308, co-morbidity 310, family history 312 and the like. The prescriptions 308 may include determining whether the human 108 is being prescribed prescriptions appropriate to the human's conditions, determining whether the human 108 is being prescribed the correct dosages of the prescriptions, determining whether the prescribed prescriptions have any undesirable interactions or contraindications, and other prescription related information. The prescriptions 308 may include a dosage engine that is invoked every time there is mention of a drug, dosage, or both. The co-morbidity 310 may include determining whether the human 108 has two or more medical conditions that may be related to an underlying cause or that have an undesirable interaction. The family history 312 may include determining whether the human's parents, siblings, or other relatives have a history of medical conditions similar to that of the human 108.

Based on determining the research into the prescriptions 308, the co-morbidity 310, and the family history 312, the second opinion module 206 may determine whether the AI response 306(1) was appropriate or whether the AI response 306(1) may be clarified. If the second opinion module 206 determines that the response 306(1) is appropriate, the second opinion module 206 does not take further action. If the second opinion module 206 determines that the response 306(1) may be clarified, then the second opinion module 206 may provide feedback 311 to the LLM 130, causing the LLM 130 to provide a clarification 316. For example, the human response 304(1) may be "Can I have soup?" and the AI response 306(1) may be "yes, you can have soup.". The clarification 316 may be "I previously said you could have soup. I noticed that either you or at least one of your family members have high blood pressure, so please check the sodium content of any pre-packaged soups and avoid soups with high sodium." In this example, "you . . . have high blood pressure" was determined by checking co-morbidity 310 and "at least one of your family members have high blood pressure" was determined by checking family history 312. As another example, the clarification 316 may be "I noticed that you are currently taking <1st prescription> in the morning. Instead of taking <2nd prescription> in the morning as I previously suggested, I suggest taking <2nd prescription> in the evening, around 12 hours after taking <1st prescription>." In this example, by checking the prescription 308, the second opinion module 206 may determine that the patient is taking the 1st prescription and that the 2nd prescription (mentioned in the AI response 306(1)) is not to be taken at the same time as the 1st prescription and instruct the LLM 130 to clarify when to take the 2nd prescription. As a further example, the clarification 316 may be "I noticed that your potassium was high in your most recent blood work. While I had previously suggested eating more avocados (for the oil), I suggest not having more than one avocado a week to avoid raising your potassium further, as avocados are high in potassium". In this example, by checking the co-morbidity 310 that includes test results (such as the results of a blood workup, e.g., comprehensive metabolic panel), the second opinion module 206 may determine that the patient has a high potassium level and that avocados are high in potassium and clarify how many avocados the human can have in a particular time frame.

In some cases, the second opinion module 206 may determine that providing the clarification 316 is insufficient and that the conversation 154 would benefit from human intervention 318. In such cases, the second opinion module 206 may use a kick out 314 engine to determine to transfer the conversation 154 to the medical professional 320 (e.g., human nurse or doctor). In addition, if the second opinion module 206 determines that a risk to the human 108 is greater than a predetermined threshold, then the second opinion module 206 may initiate a request for a third opinion 322 in which a human (e.g., a doctor, such as a specialist) reviews the human's case and takes appropriate action (e.g., provides a call (to the human 108) to clarify 324 the situation). The kick out engine will be invoked for qualitative statements that suggest symptoms that require further evaluation.

While the LLM 130 is engaged in the conversation 154 (e.g., the responses 304, 306), one or more background processes may perform data extraction 326 to extract data 330 (e.g., pertinent information, such as facts) to create a conversation summary 328 which is stored in the form of a knowledge graph 332 (or another type of data structure). The conversation summary 328 and the data 330 may enable the LLM 130 to quickly access earlier information in a lengthy conversation. With medical-related AI, conversations may be lengthy and involve many turns (e.g., 50 to 100 turns is common and the conversation may, in some cases, include 200 or even 300 turns). In such a lengthy conversations, the human 108 may reference previously provided information ("referenced information") in a current response. If the referenced information was provided early in the conversation, a conventional virtual assistant may have "forgotten" the referenced information and thus provide responses that are frustrating to the human. Alternatively, a conventional virtual assistant may have to scan through a transcript of the conversation to determine the referenced information. Such a scan may cause a lengthy delay and introduce latency into the conversation 154. By performing data extraction 326 and creating the conversation summary 328 and maintaining the knowledge graph 332 storing the data 330, the LLM 130 is able to quickly access the information (data 330) referenced by the human, thereby reducing latency. The purpose of reducing latency is to provide a natural sounding conversation and prevent the human from hanging up (i) in frustration or (ii) due to the human erroneously concluding that the conversation has concluded or the virtual assistant has encountered an error.

Thus, a low latency architecture for a conversational AI includes an AI, such as an LLM, engaged in a conversation with the human. While the AI is engaged in the conversation with the human, a second opinion module does a more in-depth analysis of information provided by the human. If the second opinion module determines that a response provided by the conversational AI is to be clarified, the second opinion module provides feedback that the conversational AI uses to provide a clarification to the human during the conversation. By parallelizing the second opinion module with the conversational AI, latency is reduced, thereby making the conversation more natural. In addition, while the conversational AI is engaged in the conversation with the human, a data extraction module (in parallel) extracts facts from each human response and creates a conversation summary in the form a data structure that can be quickly searched, such as a knowledge graph. The conversational AI can quickly access the conversation summary to look up information previously provided by the human that the human is referencing in a current turn in the conversation. The access to the conversation summary enables the conversational AI to reduce latency because the conversation AI is not pausing the conversation to perform a search of a transcript of the conversation.

Figure 4:
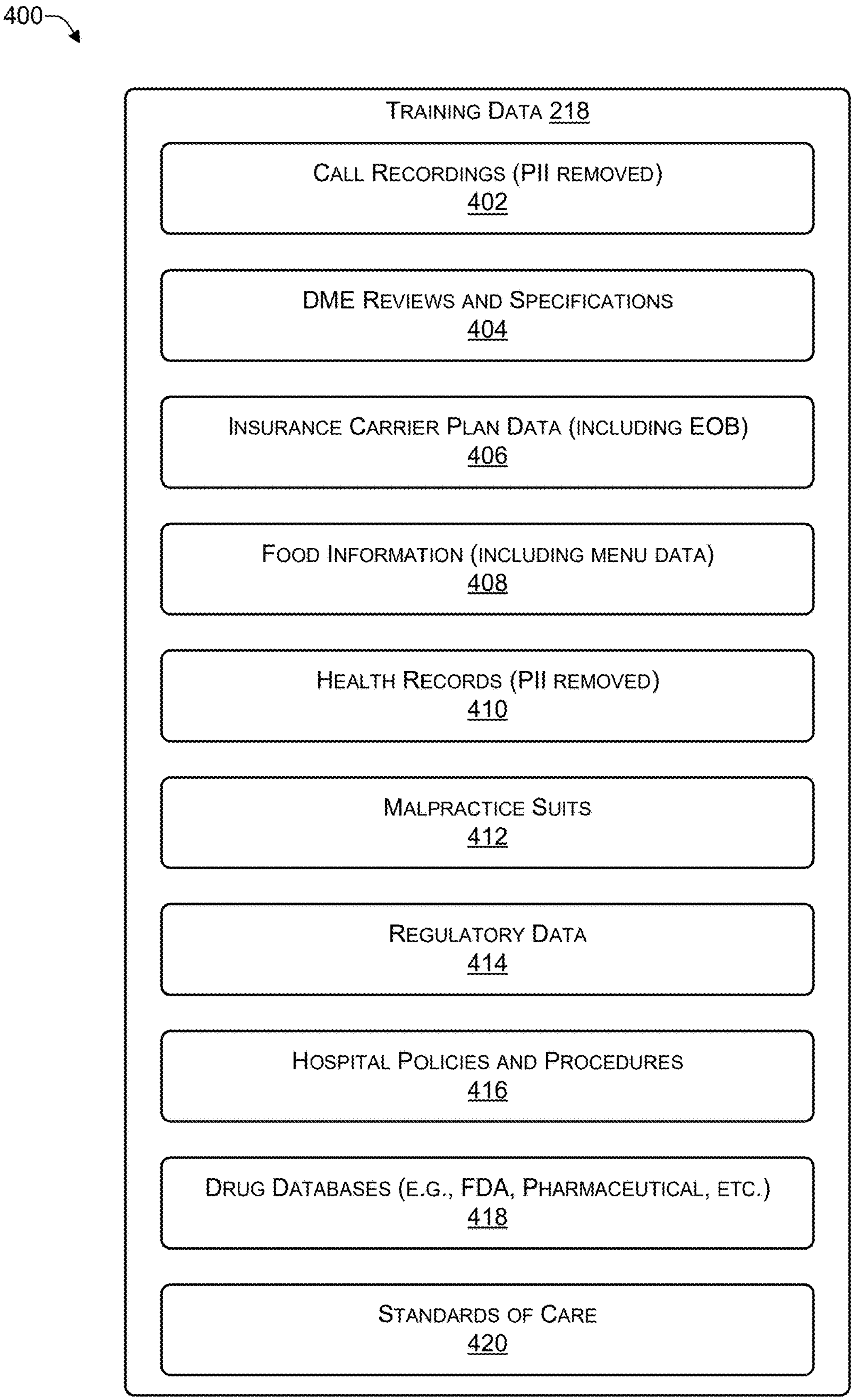
FIG. 4 is a block diagram illustrating components of training data, according to some implementations.

FIG. 4 is a block diagram 400 illustrating components of training data, according to some implementations. The training data 218 may include call recordings 402 between humans and human representatives of a healthcare provider from which personally identifiable information (PII) has been removed. The training data one 218 may include durable medical equipment (DME) reviews and specifications 404 for products ordered or prescribed by a health care provider for use by a human. The training data 218 and may include insurance carrier plan data including an explanation of benefits (EOB) and other insurance related information. The training data 218 may include food information, such as menu data, including a breakdown of various components of various food items, such as amounts (and percentages) of protein, carbohydrates, sodium, and the like. The training data 218 may include health records from which personally identifiable information (PII) has been removed. The training data 218 may include malpractice suit-related data 412, regulatory data 414, and hospital policies and procedures 416. The training data 218 may include data from drug databases 418, such as databases maintained by the food and drug administration (FDA), pharmaceutical companies, and the like. The training data 218 may include standards of care 420, such as guidelines that are generally accepted in the medical community for the treatment of a disease or a condition.

Figure 5:
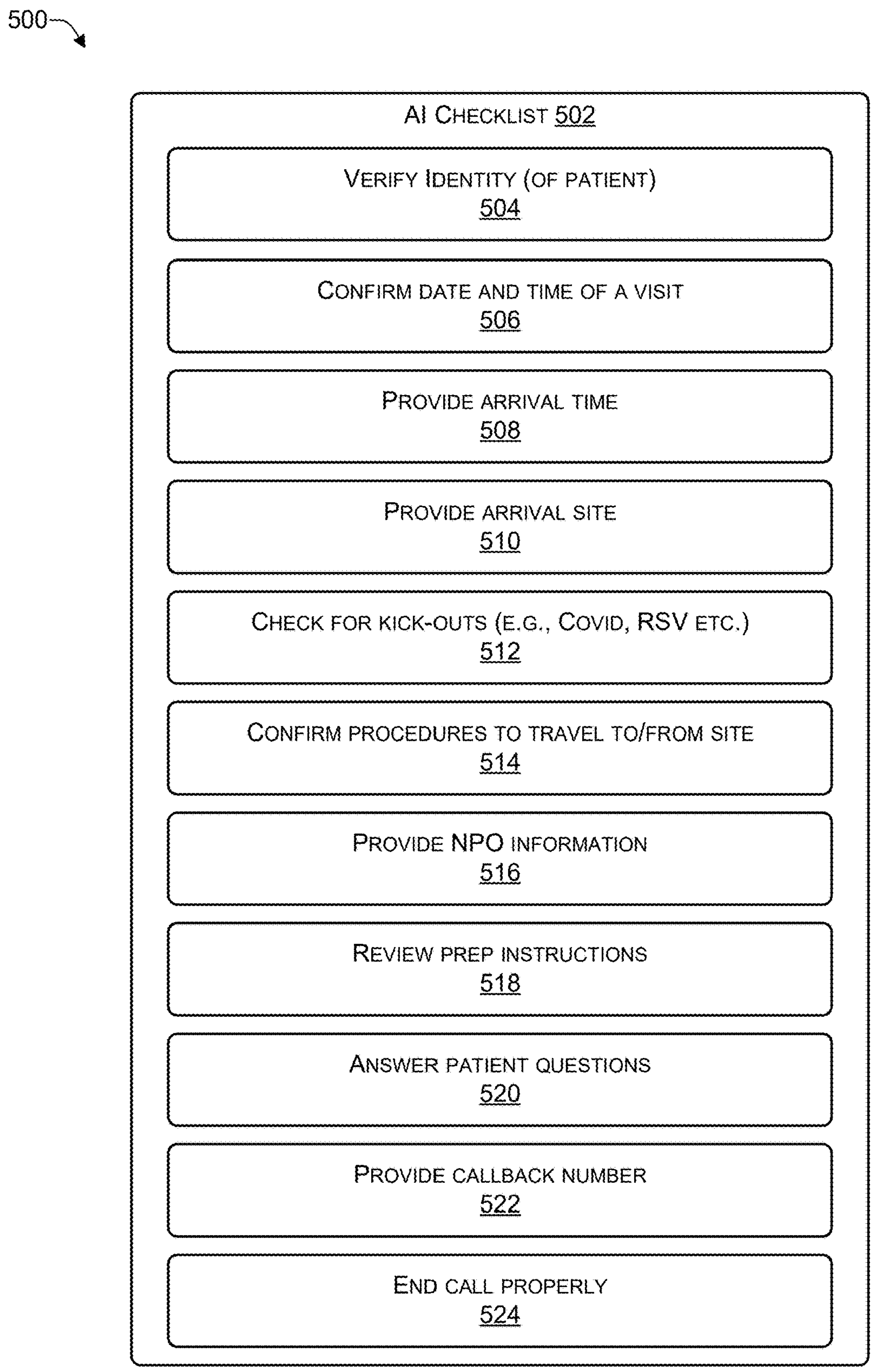
FIG. 5 is a block diagram illustrating an AI checklist, according to some implementations.

FIG. 5 is a block diagram 500 illustrating an AI checklist, according to some implementations. An AI checklist 502 that may be used by the task completion engine 226 of FIG. 2 to complete a set of tasks during a conversation with a human.

The AI checklist 502 may include verifying an identity of the human 504, confirming date and time of a visit (e.g., to a medical facility) 506, providing arrival time 508, providing information about an arrival site 510, checking for kick outs 512 by checking for conditions that when present may cause the human visit to be delayed, such as the human having an infectious disease, such as Covid, Respiratory syncytial virus (RSV), cold, flu, or the like. The AI checklist 502 may include confirming procedures to travel to and from the site 514, such as whether the human should arrange to be driven to and/or from the site. The AI checklist 502 may include providing NPO (from the Latin nil per os, which means "nothing by mouth") information 516 (e.g., what can and cannot be consumed by the human prior to a visit). The AI checklist 502 may include reviewing prep instructions 518, such as foods to eat before the visit, foods not to eat before the visit, liquids to drink before the visit, liquids not to drink before the visit, what to wear before the visit, what to bring to the visit, and so on. The AI checklist 502 may include answering human questions 520, providing a call back number 522, and ending the call properly 524, including summarizing next steps, saying goodbye. The AI checklist 502 may include outputting some or all of the interaction in a form suitable for input to an electronic health records (EHR) platform, and may be integrated with an EHR platform.

Figure 6:
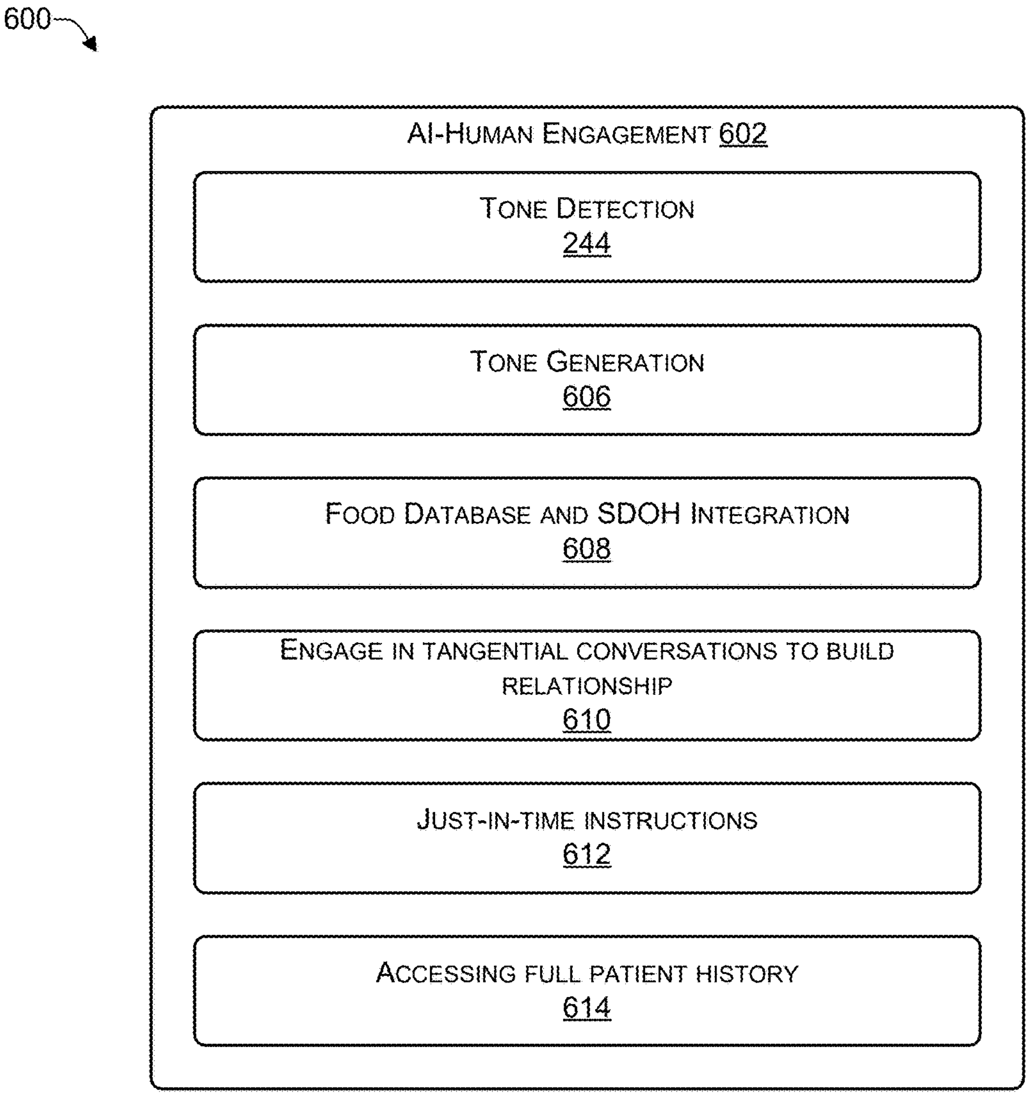
FIG. 6 is a block diagram illustrating AI-human engagement, according to some implementations.

FIG. 6 is a block diagram 600 illustrating AI-human engagement 602, according to some implementations. The AI-human engagement 602 may include tone detection 244 and tone generation 606. The AI (LLM 130) may detect a particular tone in the human's utterances and generate a similar or complementary tone. For example, if the tone of the human's utterances indicates that the human is getting angry, agitated, frustrated, or the like, then the AI may adopt a tone designed to calm the human and decrease the anger, agitation, frustration, or the like. As another example, if the tone of the human's utterances indicates that the human is calm, happy, content, or the like, then the AI may adopt a tone similar to that of the human. The term "tone" as used herein refers to a pitch (e.g., frequency) and inflection (of words and phrases) and cadence (e.g., speed of speaking) along with the words and phrases selected or output in the audio data provided to the human during the AI's turn in the conversation.

The AI-human engagement 602 may include integrating with a food database and determining social detriments of health (SDOH) 608. For example, the AI may provide dietary suggestions based on an existing diagnosis and/or medical recommendations. SDOH includes socio-economic conditions that influence the human's health, such as living conditions, working conditions, and the like.

The AI-human engagement 602 may include the AI engaging in tangential conversations to build a relationship or rapport with the human. For example, the LLM may tell jokes, or discuss hobbies or based on accessing data associated with a particular human, the AI may engage in a tangential conversation, such as inquiring about a child/parent or the like.

The AI-human engagement 602 may include the AI providing just-in-time instructions. For example, the AI may provide pre-op details at an appropriate time prior to the human visiting a medical facility for medical procedure and may provide post-op details at appropriate times after the procedure has been completed. In this way, the human is not overwhelmed with information that may be too early or too late to be currently applicable to the human.

The AI-human engagement 602 may include the AI accessing the human's history or profile prior to performing tone generation 606, accessing the food database and STO H608, engaging in tangential conversations 610, providing just-in-time construction 612 or any combination thereof.

Figure 7:
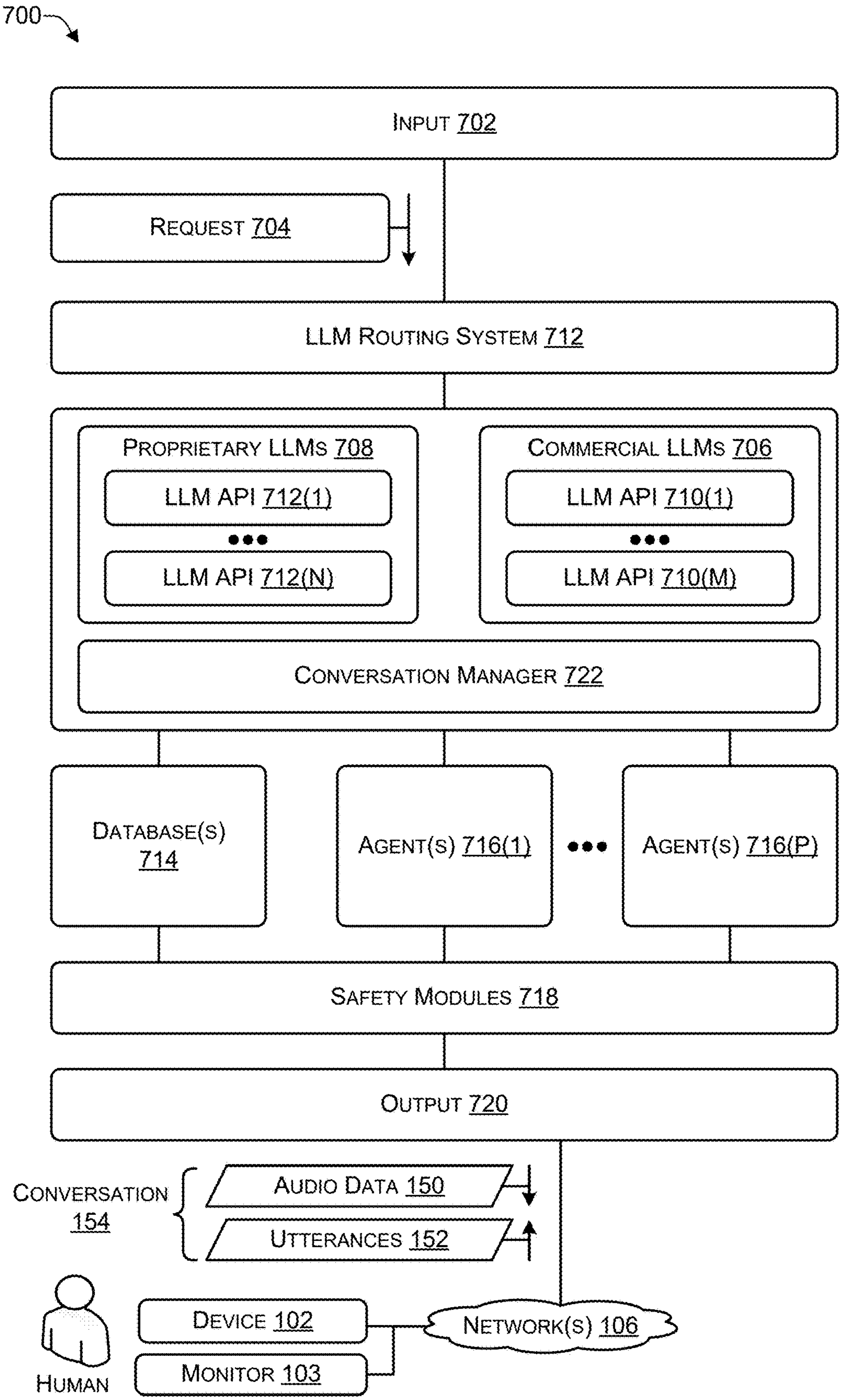
FIG. 7 is a block diagram of system that includes an LLM routing system, according to some implementations.

FIG. 7 is a block diagram of system 700 that includes an LLM routing system, according to some implementations. FIG. 7 illustrates an example conversational AI system, according to some implementations. In some examples, the system 700 can be implemented using one or more servers that collectively implement processes for enabling examples as described. In variations, system 100 can be implemented in part using client or user devices, such that an architecture described with an example of FIG. 1 is distributed. Further, with reference to FIG. 1, the system illustrates an LLM-based architecture to process system input and generate output. The system 100 can be implemented for a variety of applications, such as, for example, medical-related applications, and applications for implementing bedside manners.

In some examples, the input of system 700 can be in multiple modalities, such as text, speech, images, audio and video. The system 700 can accept input from a variety of sources, such as users, sensors, and other systems. Further, the system 700 may use a commercial (off-the-shelf) large language model (LLM) 706 (that has been trained with specific data) to process the system input 702. The LLM 706 can be used to understand the input 702, generate text, translate languages, and answer questions. In some examples, the system 700 may use a proprietary LLM 708 instead of or in addition to the commercial LLM 706. The proprietary LLM 708 can be trained on a specific dataset to improve its performance for a particular task.

In some examples, the system 700 can use an LLM application programming interface (API) to access the LLMs 706, 708. For example, LLM APIs 710(1) to 710(M) (M>0) may be used to access commercial LLMs 706. The LLM APIs 712(1) to 712(N) (N>0) may be used to access the proprietary LLMs 708. The LLM APIs 710, 712 can be used to send requests to the LLMs 706, 708 and receive responses from the LLMs 706, 708. The system 700 can use a proprietary LLM routing system 712 to route requests, such as a representative request 704 to the appropriate LLMs 706, 708. The LLM routing system 712 can be used to improve the performance and efficiency of the system 700 by routing requests to the LLMs 706, 708 that are best suited for the task associated with the request 704.

Further, in examples, the system 700 can use one or more databases 714 to store data. The data can be stored in a variety of formats, such as text, images, and video. The system 700 can use a variety of tools and agents 716(1) to 716(P) (P>0) to perform tasks. The tools and agents 716 can be used to generate text, translate languages, answer questions, and perform other tasks. The system 700 can use safety modules 718 to prevent the system from performing unsafe actions. The safety modules 718 can be used to prevent the system 700 from generating text that is harmful, offensive, illegal, or the like and that complies with various medical standards.

The system 700 can generate output 720 in multiple modalities, such as text, speech, images, and video. The output 720 can be sent to a variety of destinations, such as users, sensors, and other systems. The output of the system 700 is combined to provide appropriate vocal utterances to the human. In examples, system 700 implements voice conversations in a healthcare setting or environment. The system 700 can incorporate multiple large language models (LLMs) 706, 708 and a conversation manager 722 to facilitate natural language interactions between humans and healthcare providers. The system 700 includes a front-end interface that is accessible via voice assistants or mobile applications. When a human initiates a conversation, the system uses automatic speech recognition (ASR) technology to transcribe the spoken input and convert it into text. The text is then processed by the conversation manager 722, which uses advanced natural language understanding (NLU) techniques to identify the intent of the human's request and route it to the appropriate LLM.

The LLMs 706, 708 may be fine-tuned for specific healthcare domains, such as cardiology, radiology, or dermatology, to ensure high accuracy and relevance of the responses. Each LLM 706, 708 is trained on a large corpus of healthcare data, including electronic health records, medical literature, and human feedback, to provide a comprehensive knowledge base for the conversation. The system 700 also includes a set of targeted sub-domain adapter models for medical coding, compliance, pharmacist, nurse practitioner, and dentist. Each domain-specific module has a distinct set of self-auditing correction mechanisms and utilizes separate knowledge retrieval databases.

The conversation manager 722 coordinates the flow of the conversation between an LLM and a human by selecting the appropriate LLM based on the human's request and ensuring a coherent and engaging dialogue. The system 700 incorporates conversational strategies, such as open-ended questions, feedback loops, and active listening techniques, to maintain human engagement and satisfaction. The system 700 implements processes and functionality to ensure that the LLM is factually accurate during conversations with humans to build trust, credibility, and reduce anxiety and stress for humans. To ensure human safety and privacy, the system 700 employs several security and compliance measures. All data can be encrypted and stored securely, and access to the system is restricted to authorized healthcare providers and staff The system 700 adheres to relevant healthcare regulations, such as the Health Insurance Portability and Accountability Act (HIPAA) and the General Data Protection Regulation (GDPR).

Among other advantages, the system 700 offers a valuable solution for natural language interactions for healthcare-related functions. By incorporating multiple LLMs 706, 708 and a conversation manager 722, the system 700 enables accurate and engaging conversations between humans and LLMs od healthcare providers, leading to improved healthcare outcomes and human satisfaction.

In cases where humans exhibit mild cognitive impairment, the system 700 provides for the LLMs 706, 708 to employ additional adaptive techniques, such as simplified language, visual aids or diagrams, repeating and/or summarizing information, and providing reminders to aid comprehension and retention. The system 700 adapts to the human's level of medical understanding, using appropriate language for effective communication. A proprietary conversational benchmark testing suite to assess the system's ability to communicate effectively and agreeably.

The system 700 implements multiple techniques to reduce latency, such as by using cached conversational elements and parallel layered processing of semantic information. The system 700 performs tone detection to identify mood information and self-modulation to respond appropriately. The system 700 can implement one or more processes to manage dialog by keeping track of existing human information from the database along with new information gathered during the course of the conversation and purposefully accomplishing particular conversational objectives (set an appointment, confirm a prescription is being taken, explain a medical bill, etc.).

The system 700 can implement one or more processes to embed user queries in a high dimensional space, classifying input within several categorical domains, in order to modify and direct it to a matched internal model as part of a pre-processing pipeline. Further, the system 700 can also develop, train, implement or otherwise use a set of safety-focused language models that function to audit the output of the core models for accuracy and agreement with scientific literature and clinical best-practices. Additionally, the system 700 can implement one or more processes to combine domain specific and general retrieval corpuses to improve performance in targeted domains (e.g., medical coding) without sacrificing performance.

Figure 8:
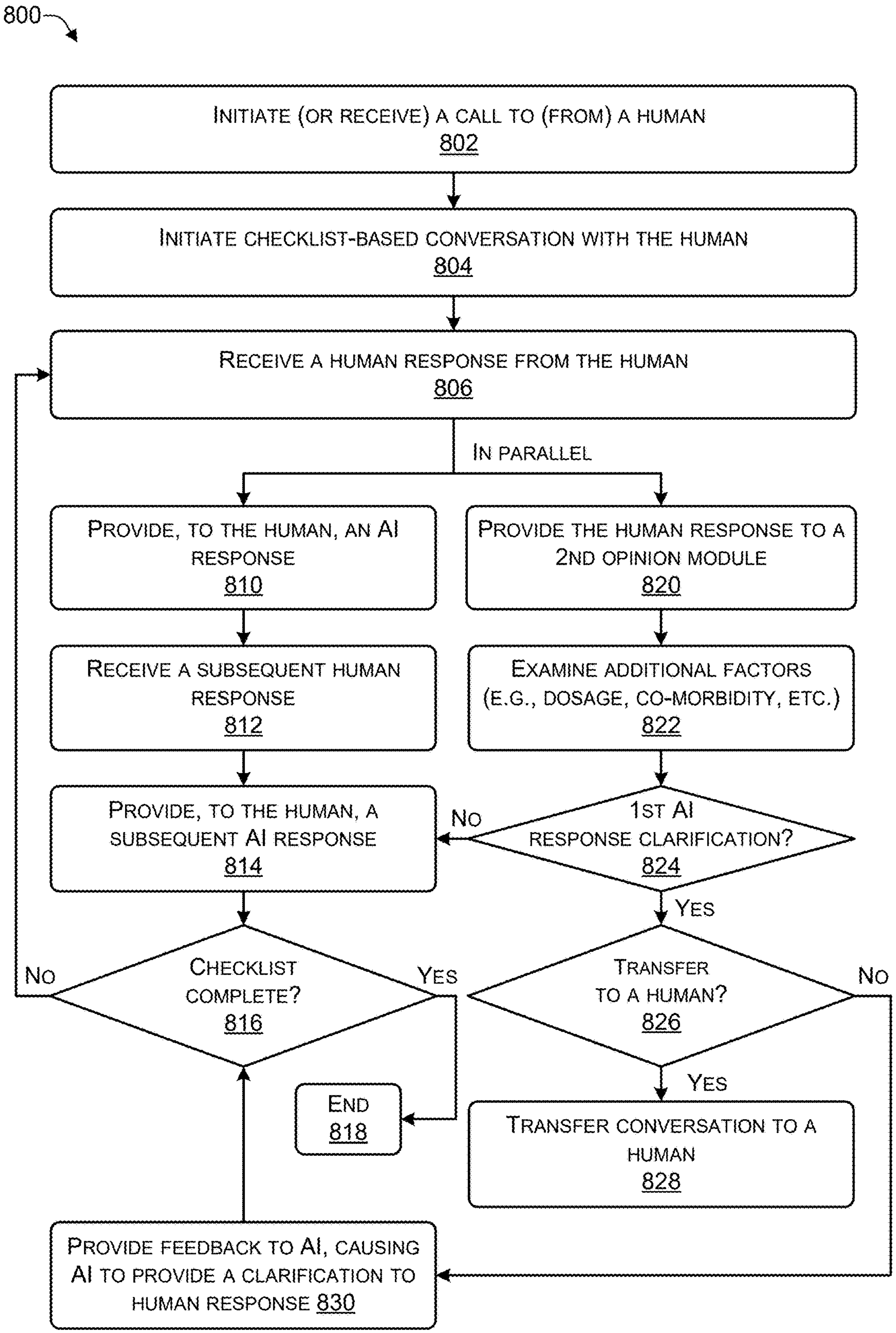
FIG. 8 is a flowchart of a process that includes analyzing a human response using a second opinion module, according to some implementations.
Figure 9:
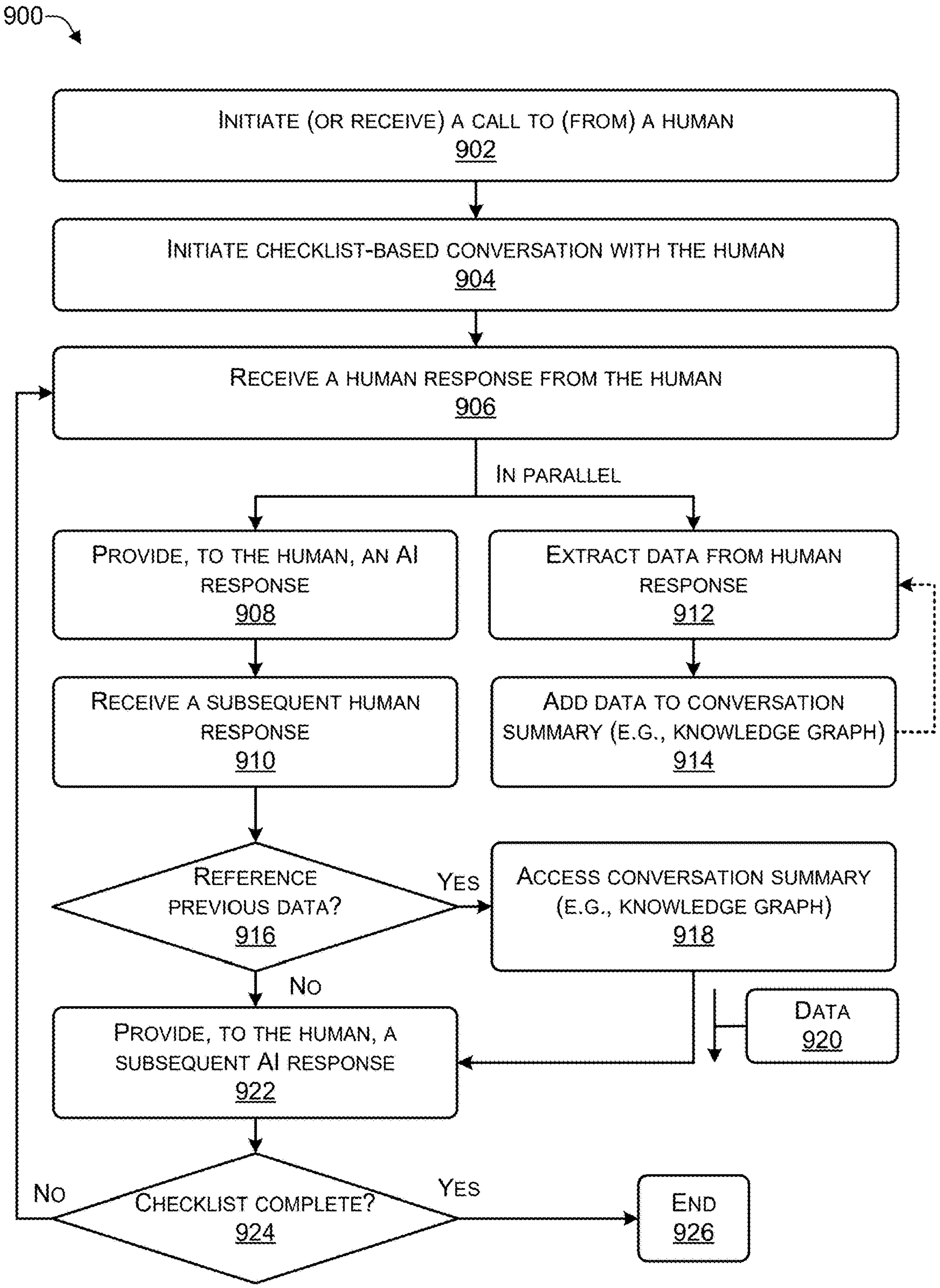
FIG. 9 is a flowchart of a process that includes accessing a conversation summary, a knowledge graph, or both, according to some implementations.
Figure 10:
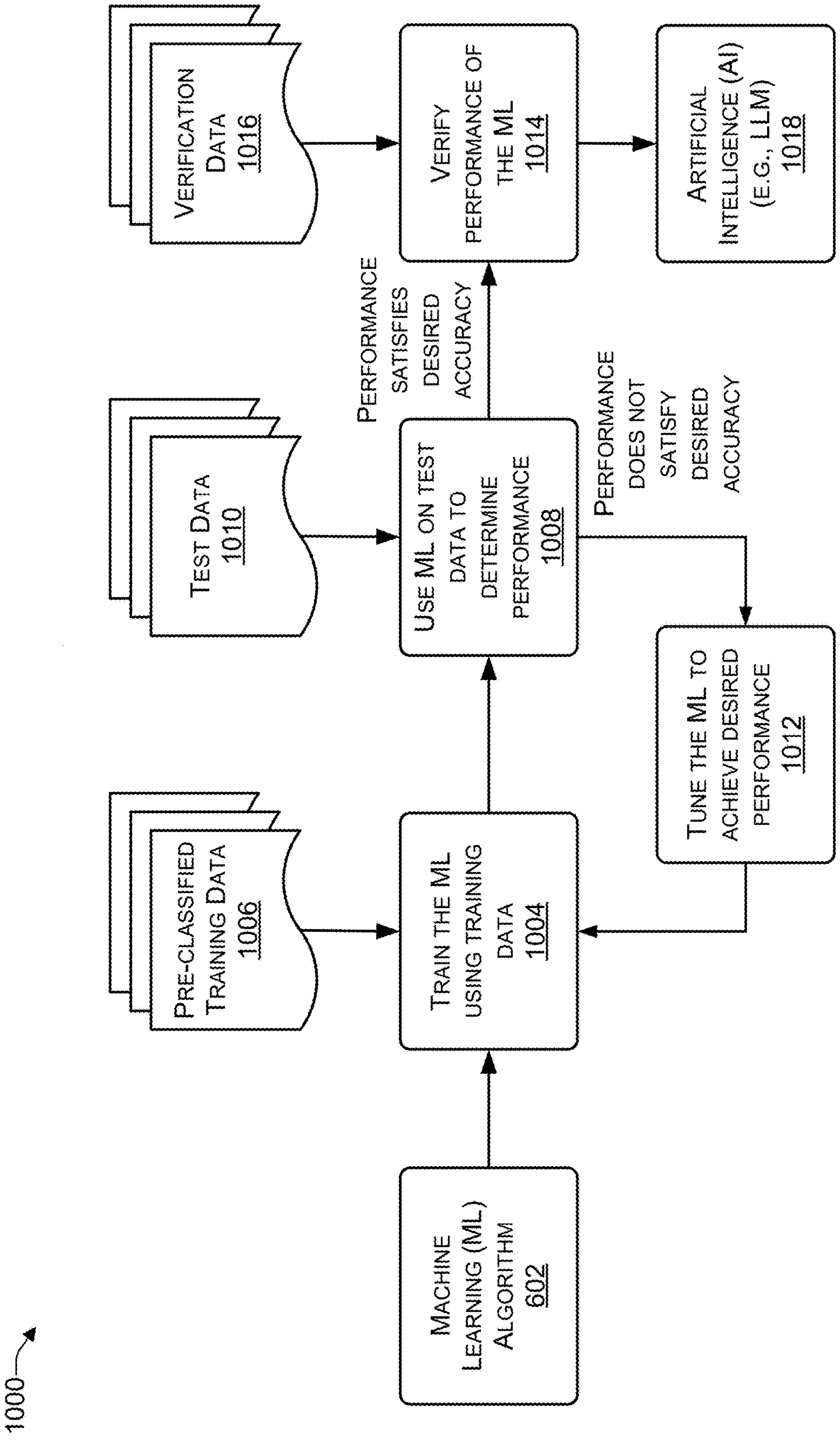
FIG. 10 is a flowchart of a process to train a machine learning algorithm, according to some implementations.

In the flow diagram of FIGS. 8, 9, and 10, each block represents one or more operations that can be implemented in hardware, software, or a combination thereof. In the context of software, the blocks represent computer-executable instructions that, when executed by one or more processors, cause the processors to perform the recited operations. Generally, computer-executable instructions include routines, programs, objects, modules, components, data structures, and the like that perform particular functions or implement particular abstract data types. The order in which the blocks are described is not intended to be construed as a limitation, and any number of the described operations can be combined in any order and/or in parallel to implement the processes. For discussion purposes, the processes 800, 900, and 1000 are described with reference to FIGS. 1, 2, 3, 4, 5, 6, and 7 as described above, although other models, frameworks, systems and environments may be used to implement these processes.

FIG. 8 is a flowchart of a process 800 that includes analyzing a human response using a second opinion module, according to some implementations. The process 800 may be performed by one or more of the LLM's 130 of FIGS. 1, 2, 3, and 7.

At 802, the process may initiate (or receive) a call to (from) a human. At 804, the process may initiate a checklist-based conversation with the human. At 806, the process may receive a human response from the human. For example, in FIG. 3, the LLM 130 may engage in the conversation 154 with the human 108. Either the LLM 130 or the human 108 may initiate a call prior to the conversation 154. The LLM 130 may use the checklist 317 to drive the conversation 154 with the human 108.

At 806, the process may receive a human response from the human. At 810, the process may provide, to the human, an AI response. At 812, the process may receive a subsequent human response. At 814, the process may provide, to the human, a subsequent AI response, and the process may proceed to 816. For example, in FIG. 3, the LLM 130 may receive the human response 304 from the human 108. The LLM 130 may provide, to the human 108, the AI response 306(1). The LLM 130 may receive a subsequent human response 304(2). The LLM 130 may provide, to the human 108, a subsequent AI response 306(2).

In parallel with 810, 812, and 814, a second opinion module (an AI) may, at 820, review the human response. At 822, the second opinion module may examine additional factors associated with the human (such as, dosage, co-morbidity, and the like). At 824, the second opinion module may determine whether the first AI response is to be clarified. If the second opinion module determines, at 824, that "no" the first AI response is not to be clarified, then the second opinion module may allow the process to continue conversing with the human. If the second opinion model module determines, at 824, that "yes" the first AI response is to be clarified, then the second opinion module may determine, at 826, whether to transfer the conversation to a human. If the second opinion module determines, at 826, that "yes" the conversation is to be transferred to a human, then, at 828, the second opinion module may transfer the conversation to a human. If the second opinion module determines, at 826, that "no" the conversation is not to be transferred to a human, then then the second opinion module may provide, at 830, feedback to the AI, causing the AI to provide a clarification (during the conversation) to the human response. The clarification may be to request additional information from the human for examination by the second opinion module. The second opinion module may then proceed to 816. For example, in FIG. 3, while the LLM 130 is engaged in the conversation 154 (e.g., responses 304(1), 306(1), 304(2), 306(2)), the second opinion module may examine the human response 304(1) in more depth/detail. For example, the second opinion module 206 may examine additional factors associated with the human 108, such as prescriptions (e.g., dosage, interactions, contraindications, or the like), co-morbidity 310, family history 312, and the like. After examining the additional factors, the second opinion module 206 may determine whether the AI response 306(1) is to be clarified. If the second opinion module 206 determines, that the AI response 306(1) is not to be clarified, then the second opinion module 206 allows the LLM 130 to continue the conversation 154 with the human 108. If the second opinion model module 206 determines that the first AI response 306(1) is to be clarified, then the second opinion module 206 may determine whether to transfer the conversation 154 to a human. If the second opinion module 206 determines that the conversation 154 is to be transferred to a human, then the second opinion module may transfer the conversation 154 to one of the medical professionals 112. If the second opinion module 206 determines that the conversation 154 is not to be transferred to a human, then then the second opinion module 206 may provide feedback 311 to the LLM 130, causing the LLM 130 to provide the clarification 316 during the conversation 154.

At 816, the process may determine whether a checklist is complete. If the process determines, at 816, that "yes" the checklist is complete, then the process may end the conversation. If the process determines, at 816 that "no" the checklist is incomplete, then the process may proceed back to 806 to receive a next human response from the human. For example, in FIG. 3, The LLM 130 may continue with the conversation 154 until the LLM 130 has completed the tasks in the checklist 317.

Thus, an AI, such as an LLM, may engage in a conversation with a human. The conversation may be initiated by the AI or by the human (e.g., human was asked to call a number that was routed to the AI). While the AI is engaged in the conversation with the human, a second opinion module does a more in-depth analysis of information provided by the human. If the second opinion module determines that a response provided by the conversational AI is to be clarified, the second opinion module provides feedback that the conversational AI uses to provide a clarification to the human during the conversation. By parallelizing the second opinion module with the conversational AI, latency is reduced, thereby making the conversation more natural while at the same time, enabling a second AI to perform a lengthier and more detailed analysis of information provided by the human.

FIG. 9 is a flowchart of a process 900 that includes accessing a conversation summary, a knowledge graph, or both, according to some implementations. The process 900 may be performed by one or more of the LLM's 130 of FIGS. 1, 2, 3, and 7. While FIGS. 8 and 9 are shown as being separate flowcharts, it should be understood that the two flowcharts should be taken together, with 802, 804 and 806 corresponding to 902, 904 and 906, respectively. FIG. 8 illustrates the second opinion module operating in parallel with the primary LLM engaging in a conversation with the human. FIG. 9 illustrates creating a conversation summary in parallel with the primary LLM engaging in a conversation with the human.

At 902, the process may initiate (or receive) a call to (from) a human. At 904, the process may initiate a checklist-based conversation with the human. For example, in FIG. 3, the LLM 130 may engage in the conversation 154 with the human 108. Either the LLM 130 or the human 108 may initiate a call prior to the conversation 154. The LLM 130 may use the checklist 317 to drive the conversation 154 with the human 108.

At 906, the process may receive a human response from the human. At 908, the process may provide, to the human, an AI response. At 910, the process may receive a subsequent human response. At 916, the process may determine whether the subsequent human response referenced previously provided data. If the process determines, at 916, that "yes" the subsequent human response references previously provided data, then, at 918, the process may access a conversation summary. In some cases, the conversation summary may be stored in the form of a knowledge graph or another type of data structure. After accessing the conversation summary, the process may access data 920, and provide to the human, at 922, a subsequent AI response (based on accessing the data 920 in the conversation summary). At 924 the process may determine whether a checklist is complete. If the process determines, at 924, that "no" the checklist is not complete, then the process may proceed back to 906 to receive an additional human response. If the process determines, at 924, that "yes" the checklist is complete, then the process may end, at 926. For example, in FIG. 3, the LLM 130 may receive the human response 304(1) from the human 108. The LLM 130 may provide, to the human 108, the AI response 306(1). The LLM 130 may receive a subsequent human response 304(2). The LLM 130 may determine whether the subsequent human response 304(2) references previously provided data. If the LLM 130 determines that the subsequent human response 304(2) references previously provided data, then the LLM 130 may access the conversation summary 328. In some cases, the conversation summary 328 may be stored in the form of the knowledge graph 332 (or another type of data structure). After accessing the conversation summary 328, the LLM 130 may provide, to the human 108, a subsequent AI response 306(2), based on accessing the data in the conversation summary. The LLM 130 may determine whether the checklist 317 is complete. If the LLM 130 determines the checklist 317 is not complete, then the LLM 130 may receive an additional human response 304. If the LLM 130 determines the checklist 317 is complete, then the LLM 130 may end the conversation 154.

In parallel with 908 and 910, a data extraction module may, at 912, extract data (e.g., facts and other pertinent information) from the human response. At 914, the data extraction module may add the data to a conversation summary. For example, the conversation summary may be stored in the form of a knowledge graph or another type of data structure. The data extraction module may repeatedly monitor the human responses received at 906, extract data from the human response, at 912, and add the data to the conversation summary, at 914. In this way, the conversation summary is kept up to date. For example, in FIG. 3, while the LLM 130 is engaged in the conversation 154 with the human 108, the data extraction module 326 may extract data 330 (e.g., facts and other pertinent information) from the human response 304(land add the data 330 to the conversation summary 328. For example, the conversation summary 328 may be stored in the form of the knowledge graph 332 or another type of data structure. The data extraction module 326 may repeatedly monitor the human responses 304, extract data 330 from the human responses 304 and add the data 330 to the conversation summary 328. In this way, the conversation summary 328 is kept up to date.

Thus, a low latency architecture for a conversational AI includes an AI, such as an LLM, engaged in a conversation with the human. While the AI is engaged in the conversation with the human, a data extraction module (in parallel) extracts facts from each human response and creates a conversation summary in the form a data structure that can be quickly searched, such as a knowledge graph. The conversational AI can quickly access the conversation summary to look up data that was previously provided by the human that the human is referencing in a current response (turn) in the conversation. The access to the conversation summary enables the conversational AI to reduce latency because the conversation AI is not pausing the conversation to perform a search of a transcript of the conversation.

FIG. 10 is a flowchart of a process 1000 to train a machine learning algorithm, according to some implementations. For example, the process 1000 may be performed during the pre-training 216 or other training described herein.

At 1002, a machine learning algorithm (e.g., software code) may be created by one or more software designers. For example, the LLMs 130 may be created by software designers. At 1004, the machine learning algorithm may be trained using pre-classified training data 1006. For example, the training data 1006 may have been pre-classified by humans, by machine learning, or a combination of both. After the machine learning has been trained using the pre-classified training data 1006, the machine learning may be tested, at 1008, using test data 1010 to determine a performance metric of the machine learning. The performance metric may include, for example, precision, recall, Frechet Inception Distance (FID), or a more complex performance metric. For example, in the case of a classifier, the accuracy of the classification may be determined using the test data 1010.

If the performance metric of the machine learning does not satisfy a desired measurement (e.g., 95%, 98%, 99% in the case of accuracy), at 1008, then the machine learning code may be tuned, at 1012, to achieve the desired performance measurement. For example, at 1012, the software designers may modify the machine learning software code to improve the performance of the machine learning algorithm. After the machine learning has been tuned, at 1012, the machine learning may be retrained, at 1004, using the pre-classified training data 1006. In this way, 1004, 1008, 1012 may be repeated until the performance of the machine learning is able to satisfy the desired performance metric. For example, in the case of a classifier, the classifier may be tuned to be able to classify the test data 1010 with the desired accuracy.

After determining, at 1008, that the performance of the machine learning satisfies the desired performance metric, the process may proceed to 1014, where verification data 1016 may be used to verify the performance of the machine learning. After the performance of the machine learning is verified, at 1014, the machine learning 1002, which has been trained to provide a particular level of performance may be used as an artificial intelligence (AI) 1018, such as the LLM 130.

Figure 11:
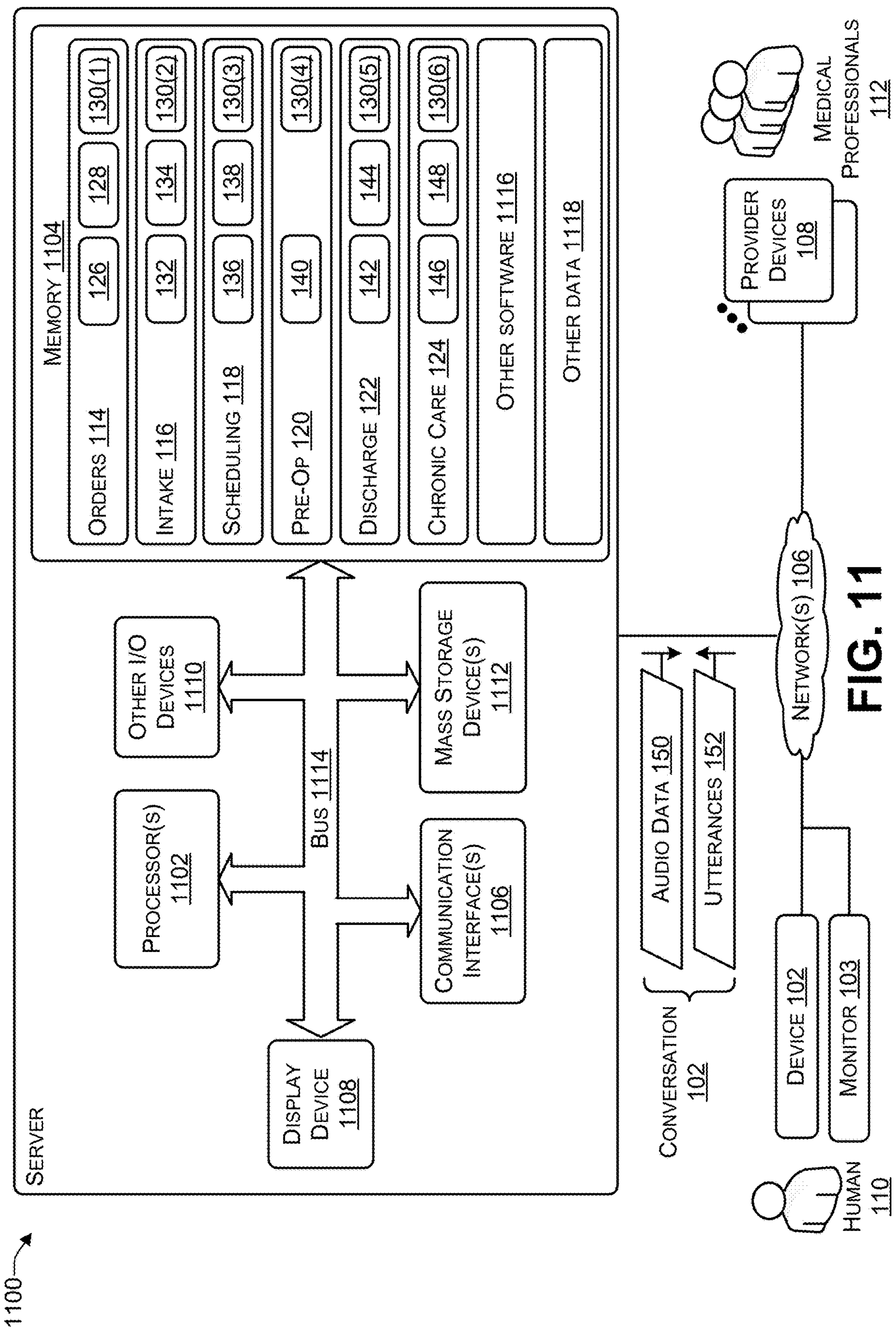
FIG. 11 illustrates an example configuration of a computing device that can be used to implement the systems and techniques described herein.

FIG. 11 illustrates an example configuration of a device 1100 that can be used to implement the systems and techniques described herein. For example, the device 1100 may be a server (or a set of servers) used to host one or more of the components described herein. In some cases, the systems and techniques described herein may be implemented as an application programming interface (API), a plugin, or another type of implementation.

The device 1100 may include one or more processors 1102 (e.g., central processing unit (CPU), graphics processing unit (GPU), or the like), a memory 1104, communication interfaces 1106, a display device 1108, other input/output (I/O) devices 1110 (e.g., keyboard, trackball, and the like), and one or more mass storage devices 1112 (e.g., disk drive, solid state disk drive, or the like), configured to communicate with each other, such as via one or more system buses 1114 or other suitable connections. While a single system bus 1114 is illustrated for ease of understanding, it should be understood that the system bus 1114 may include multiple buses, such as a memory device bus, a storage device bus (e.g., serial ATA (SATA) and the like), data buses (e.g., universal serial bus (USB) and the like), video signal buses (e.g., ThunderBolt®, digital video interface (DVI), high definition media interface (HDMI), and the like), power buses, etc.

The processors 1102 are one or more hardware devices that may include a single processing unit or a number of processing units, all of which may include single or multiple computing units or multiple cores. The processors 1102 may include a graphics processing unit (GPU) that is integrated into the CPU or the GPU may be a separate processor device from the CPU. The processors 1102 may be implemented as one or more microprocessors, microcomputers, microcontrollers, digital signal processors, central processing units, graphics processing units, state machines, logic circuitries, and/or any devices that manipulate signals based on operational instructions. Among other capabilities, the processors 1102 may be configured to fetch and execute computer-readable instructions stored in the memory 1104, mass storage devices 1112, or other computer-readable media.

Memory 1104 and mass storage devices 1112 are examples of computer storage media (e.g., memory storage devices) for storing instructions that can be executed by the processors 1102 to perform the various functions described herein. For example, memory 1104 may include both volatile memory and non-volatile memory (e.g., random access memory (RAM), read only memory (ROM), or the like) devices. Further, mass storage devices 1112 may include hard disk drives, solid-state drives, removable media, including external and removable drives, memory cards, flash memory, floppy disks, optical disks (e.g., compact disc (CD), digital versatile disc (DVD), a storage array, a network attached storage (NAS), a storage area network (SAN), or the like. Both memory 1104 and mass storage devices 1112 may be collectively referred to as memory or computer storage media herein and may be any type of non-transitory media capable of storing computer-readable, processor-executable program instructions as computer program code that can be executed by the processors 1102 as a particular machine configured for carrying out the operations and functions described in the implementations herein.

The device 1100 may include one or more communication interfaces 1106 for exchanging data via the network 110. The communication interfaces 1106 can facilitate communications within a wide variety of networks and protocol types, including wired networks (e.g., Ethernet, Data Over Cable Service Interface Specification (DOCSIS), digital subscriber line (DSL), Fiber, universal serial bus (USB) etc.) and wireless networks (e.g., wireless local area network (WLAN), global system for mobile (GSM), code division multiple access (CDMA), 802.11, Bluetooth, Wireless USB, ZigBee, cellular, satellite, etc.), the Internet and the like. Communication interfaces 1106 can also provide communication with external storage, such as a storage array, network attached storage, storage area network, cloud storage, or the like.

The display device 1108 may be used for displaying content (e.g., information and images) to users. Other I/O devices 1110 may be devices that receive various inputs from a user and provide various outputs to the user, and may include a keyboard, a touchpad, a mouse, a gaming controller (e.g., joystick, steering controller, accelerator pedal, brake pedal controller, virtual reality (VR) headset, VR glove, or the like), a printer, audio input/output devices, and so forth.

The computer storage media, such as memory 1104 and mass storage devices 1112, may be used to store any of the software and data described herein.

The example systems and computing devices described herein are merely examples suitable for some implementations and are not intended to suggest any limitation as to the scope of use or functionality of the environments, architectures and frameworks that can implement the processes, components and features described herein. Thus, implementations herein are operational with numerous environments or architectures, and may be implemented in general purpose and special-purpose computing systems, or other devices having processing capability. Generally, any of the functions described with reference to the figures can be implemented using software, hardware (e.g., fixed logic circuitry) or a combination of these implementations. The term "module," "mechanism" or "component" as used herein generally represents software, hardware, or a combination of software and hardware that can be configured to implement prescribed functions. For instance, in the case of a software implementation, the term "module," "mechanism" or "component" can represent program code (and/or declarative-type instructions) that performs specified tasks or operations when executed on a processing device or devices (e.g., CPUs or processors). The program code can be stored in one or more computer-readable memory devices or other computer storage devices. Thus, the processes, components and modules described herein may be implemented by a computer program product.

Furthermore, this disclosure provides various example implementations, as described and as illustrated in the drawings. However, this disclosure is not limited to the implementations described and illustrated herein, but can extend to other implementations, as would be known or as would become known to those skilled in the art. Reference in the specification to "one implementation," "this implementation," "these implementations" or "some implementations" means that a particular feature, structure, or characteristic described is included in at least one implementation, and the appearances of these phrases in various places in the specification are not necessarily all referring to the same implementation.

Although the present technology disclosed has been described in connection with several implementations, the technology disclosed is not intended to be limited to the specific forms set forth herein. On the contrary, it is intended to cover such alternatives, modifications, and equivalents as can be reasonably included within the scope of the technology disclosed as defined by the appended claims.

Some implementations of the technology disclosed relate to using a Transformer model to provide a multi-turn conversational system. In particular, the technology disclosed proposes a parallel input, parallel output (PIPO) multi-turn conversational system based on the Transformer architecture. The Transformer model relies on a self-attention mechanism to compute a series of context-informed vector-space representations of elements in the input sequence and the output sequence, which are then used to predict distributions over subsequent elements as the model predicts the output sequence element-by-element. Not only is this mechanism straightforward to parallelize, but as each input's representation is also directly informed by all other inputs' representations, this results in an effectively global receptive field across the whole input sequence. This stands in contrast to, e.g., convolutional architectures which typically only have a limited receptive field.

In one implementation, the disclosed multi-turn conversational system is a multilayer perceptron (MLP). In another implementation, the disclosed multi-turn conversational system is a feedforward neural network. In yet another implementation, the disclosed multi-turn conversational system is a fully connected neural network. In a further implementation, the disclosed multi-turn conversational system is a fully convolution neural network. In a yet further implementation, the disclosed multi-turn conversational system is a semantic segmentation neural network. In a yet another further implementation, the disclosed multi-turn conversational system is a generative adversarial network (GAN) (e.g., CycleGAN, StyleGAN, pixelRNN, text-2-image, DiscoGAN, IsGAN). In a yet another implementation, the disclosed multi-turn conversational system includes self-attention mechanisms like Transformer, Vision Transformer (ViT), Bidirectional Transformer (BERT), Detection Transformer (DETR), Deformable DETR, UP-DETR, DeiT, Swin, GPT, iGPT, GPT-2, GPT-3, various ChatGPT versions, various LLaMA versions, BERT, SpanBERT, RoBERTa, XLNet, ELECTRA, UniLM, BART, T5, ERNIE (THU), KnowBERT, DeiT-Ti, DeiT-S, DeiT-B, T2T-ViT-14, T2T-ViT-19, T2T-ViT-24, PVT-Small, PVT-Medium, PVT-Large, TNT-S, TNT-B, CPVT-S, CPVT-S-GAP, CPVT-B, Swin-T, Swin-S, Swin-B, Twins-SVT-S, Twins-SVT-B, Twins-SVT-L, Shuffle-T, Shuffle-S, Shuffle-B, XCiT-S12/16, CMT-S, CMT-B, VOLO-D1, VOLO-D2, VOLO-D3, VOLO-D4, MoCo v3, ACT, TSP, Max-DeepLab, VisTR, SETR, Hand-Transformer, HOT-Net, METRO, Image Transformer, Taming transformer, TransGAN, IPT, TTSR, STTN, Masked Transformer, CLIP, DALL-E, Cogview, UniT, ASH, TinyBert, FullyQT, ConvBert, FCOS, Faster R-CNN+FPN, DETR-DC5, TSP-FCOS, TSP-RCNN, ACT+MKDD (L=32), ACT+MKDD (L=16), SMCA, Efficient DETR, UP-DETR, UP-DETR, ViTB/16-FRCNN, ViT-B/16-FRCNN, PVT-Small+RetinaNet, Swin-T+RetinaNet, Swin-T+ATSS, PVT-Small+DETR, TNT-S+DETR, YOLOS-Ti, YOLOS-S, and YOLOS-B.

In one implementation, the disclosed multi-turn conversational system is a convolution neural network (CNN) with a plurality of convolution layers. In another implementation, the disclosed multi-turn conversational system is a recurrent neural network (RNN) such as a long short-term memory network (LSTM), bi-directional LSTM (Bi-LSTM), or a gated recurrent unit (GRU). In yet another implementation, the disclosed multi-turn conversational system includes both a CNN and an RNN.

In yet other implementations, the disclosed multi-turn conversational system can use 1D convolutions, 2D convolutions, 3D convolutions, 4D convolutions, 5D convolutions, dilated or atrous convolutions, transpose convolutions, depthwise separable convolutions, pointwise convolutions, 1×1 convolutions, group convolutions, flattened convolutions, spatial and cross-channel convolutions, shuffled grouped convolutions, spatial separable convolutions, and deconvolutions. The disclosed multi-turn conversational system can use one or more loss functions such as logistic regression/log loss, multi-class cross-entropy/softmax loss, binary cross-entropy loss, mean-squared error loss, L1 loss, L2 loss, smooth L1 loss, and Huber loss. The disclosed multi-turn conversational system can use any parallelism, efficiency, and compression schemes such TFRecords, compressed encoding (e.g., PNG), sharding, parallel calls for map transformation, batching, prefetching, model parallelism, data parallelism, and synchronous/asynchronous stochastic gradient descent (SGD). The disclosed multi-turn conversational system can include upsampling layers, downsampling layers, recurrent connections, gates and gated memory units (like an LSTM or GRU), residual blocks, residual connections, highway connections, skip connections, peephole connections, activation functions (e.g., non-linear transformation functions like rectifying linear unit (ReLU), leaky ReLU, exponential liner unit (ELU), sigmoid and hyperbolic tangent (tanh)), batch normalization layers, regularization layers, dropout, pooling layers (e.g., max or average pooling), global average pooling layers, and attention mechanisms.

The disclosed multi-turn conversational system can be a linear regression model, a logistic regression model, an Elastic Net model, a support vector machine (SVM), a random forest (RF), a decision tree, and a boosted decision tree (e.g., XGBoost), or some other tree-based logic (e.g., metric trees, kd-trees, R-trees, universal B-trees, X-trees, ball trees, locality sensitive hashes, and inverted indexes). The disclosed multi-turn conversational system can be an ensemble of multiple models, in some implementations.

In some implementations, the disclosed multi-turn conversational system can be trained using backpropagation-based gradient update techniques. Example gradient descent techniques that can be used for training the disclosed multi-turn conversational system include stochastic gradient descent, batch gradient descent, and mini-batch gradient descent. Some examples of gradient descent optimization algorithms that can be used to train the disclosed multi-turn conversational system are Momentum, Nesterov accelerated gradient, Adagrad, Adadelta, RMSprop, Adam, AdaMax, Nadam, and AMSGrad.

Transformer Logic

Machine learning is the use and development of computer systems that can learn and adapt without following explicit instructions, by using algorithms and statistical models to analyze and draw inferences from patterns in data. Some of the state-of-the-art models use Transformers, a more powerful and faster model than neural networks alone. Transformers originate from the field of natural language processing (NLP), but can be used in computer vision and many other fields. Neural networks process input in series and weight relationships by distance in the series. Transformers can process input in parallel and do not necessarily weigh by distance. For example, in natural language processing, neural networks process a sentence from beginning to end with the weights of words close to each other being higher than those further apart. This leaves the end of the sentence very disconnected from the beginning causing an effect called the vanishing gradient problem. Transformers look at each word in parallel and determine weights for the relationships to each of the other words in the sentence. These relationships are called hidden states because they are later condensed for use into one vector called the context vector. Transformers can be used in addition to neural networks. This architecture is described here.

Encoder-Decoder Architecture

Figure 12:
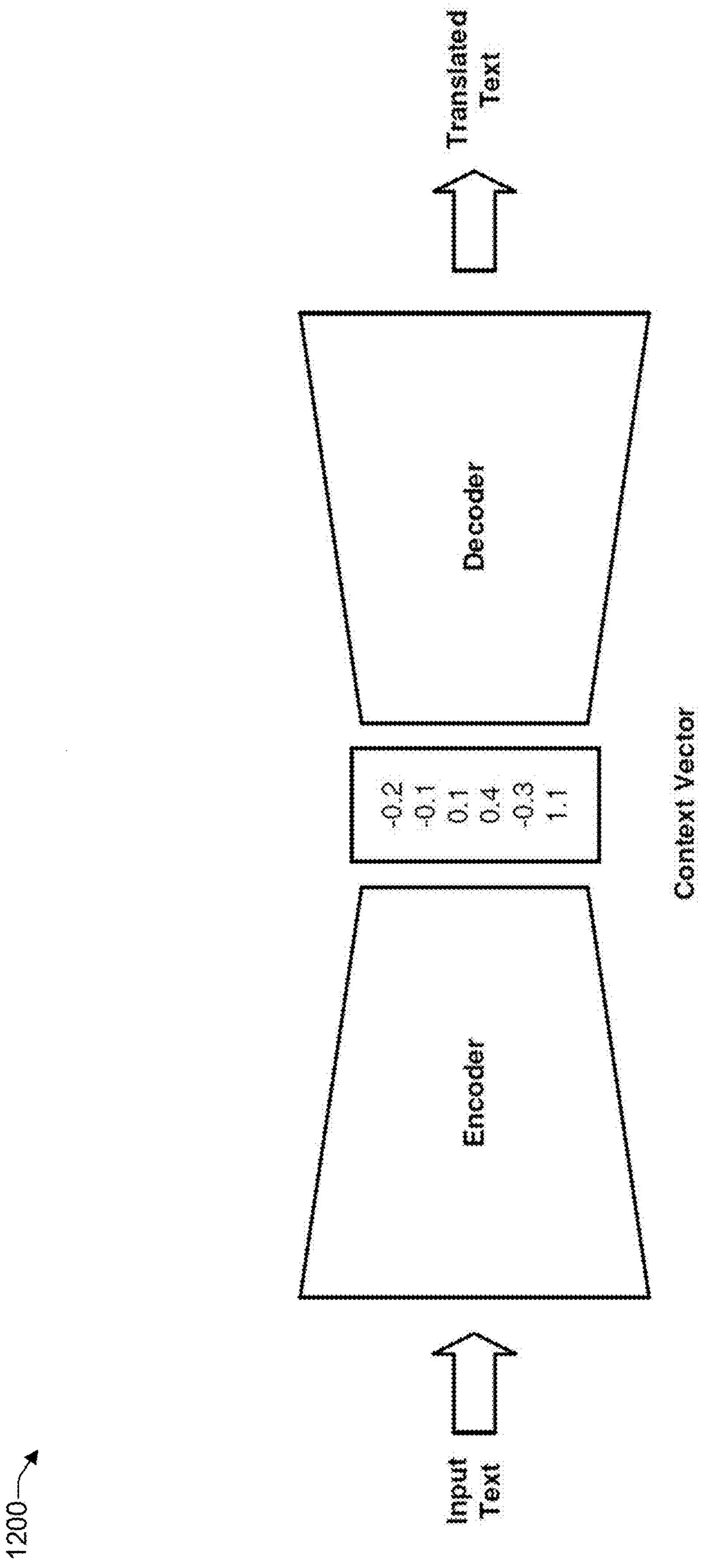
FIG. 12 is a schematic representation of an encoder-decoder architecture.

FIG. 12 is a schematic representation 1200 of an encoder-decoder architecture. This architecture is often used for NLP and has two main building blocks. The first building block is the encoder that encodes an input into a fixed-size vector. In the system we describe here, the encoder is based on a recurrent neural network (RNN). At each time step, t, a hidden state of time step, t−1, is combined with the input value at time step t to compute the hidden state at timestep t. The hidden state at the last time step, encoded in a context vector, contains relationships encoded at all previous time steps. For NLP, each step corresponds to a word. Then the context vector contains information about the grammar and the sentence structure. The context vector can be considered a low-dimensional representation of the entire input space. For NLP, the input space is a sentence, and a training set consists of many sentences.

The context vector is then passed to the second building block, the decoder. For translation, the decoder has been trained on a second language. Conditioned on the input context vector, the decoder generates an output sequence. At each time step, t, the decoder is fed the hidden state of time step, t−1, and the output generated at time step, t−1. The first hidden state in the decoder is the context vector, generated by the encoder. The context vector is used by the decoder to perform the translation.

The whole model is optimized end-to-end by using backpropagation, a method of training a neural network in which the initial system output is compared to the desired output and the system is adjusted until the difference is minimized. In backpropagation, the encoder is trained to extract the right information from the input sequence, the decoder is trained to capture the grammar and vocabulary of the output language. This results in a fluent model that uses context and generalizes well. When training an encoder-decoder model, the real output sequence is used to train the model to prevent mistakes from stacking. When testing the model, the previously predicted output value is used to predict the next one.

When performing a translation task using the encoder-decoder architecture, all information about the input sequence is forced into one vector, the context vector. Information connecting the beginning of the sentence with the end is lost, the vanishing gradient problem. Also, different parts of the input sequence are important for different parts of the output sequence, information that cannot be learned using only RNNs in an encoder-decoder architecture.

Attention Mechanism

Figure 13:
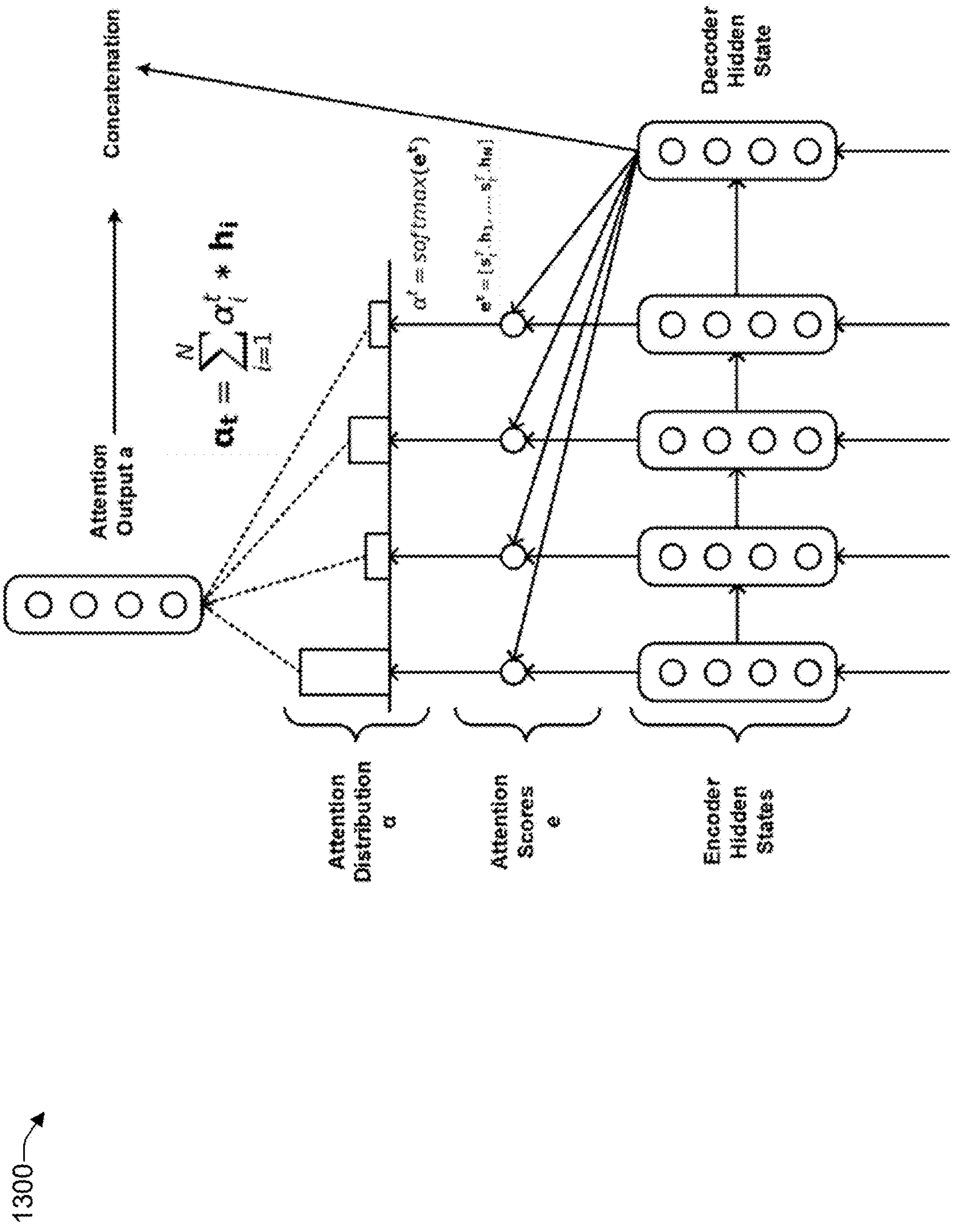
FIG. 13 shows an overview of an attention mechanism added onto an RNN encoder-decoder architecture.

Attention mechanisms distinguish Transformers from other machine learning models. The attention mechanism provides a solution for the vanishing gradient problem. FIG. 13 shows an overview 1300 of an attention mechanism added onto an RNN encoder-decoder architecture. At every step, the decoder is given an attention score, e, for each encoder hidden state. In other words, the decoder is given weights for each relationship between words in a sentence. The decoder uses the attention score concatenated with the context vector during decoding. The output of the decoder at time step t is based on all encoder hidden states and the attention outputs. The attention output captures the relevant context for time step t from the original sentence. Thus, words at the end of a sentence may now have a strong relationship with words at the beginning of the sentence. In the sentence "The quick brown fox, upon arriving at the doghouse, jumped over the lazy dog," fox and dog can be closely related despite being far apart in this complex sentence.

To weight encoder hidden states, a dot product between the decoder hidden state of the current time step, and all encoder hidden states, is calculated. This results in an attention score for every encoder hidden state. The attention scores are higher for those encoder hidden states that are similar to the decoder hidden state of the current time step. Higher values for the dot product indicate the vectors are pointing more closely in the same direction. The attention scores are converted to fractions that sum to one using the SoftMax function.

The SoftMax scores provide an attention distribution. The x-axis of the distribution is position in a sentence. The y-axis is attention weight. The scores show which encoder hidden states are most closely related. The SoftMax scores specify which encoder hidden states are the most relevant for the decoder hidden state of the current time step.

The elements of the attention distribution are used as weights to calculate a weighted sum over the different encoder hidden states. The outcome of the weighted sum is called the attention output. The attention output is used to predict the output, often in combination (concatenation) with the decoder hidden states. Thus, both information about the inputs, as well as the already generated outputs, can be used to predict the next outputs.

By making it possible to focus on specific parts of the input in every decoder step, the attention mechanism solves the vanishing gradient problem. By using attention, information flows more directly to the decoder. It does not pass through many hidden states. Interpreting the attention step can give insights into the data. Attention can be thought of as a soft alignment. The words in the input sequence with a high attention score align with the current target word. Attention describes long-range dependencies better than RNN alone. This enables analysis of longer, more complex sentences.

The attention mechanism can be generalized as: given a set of vector values and a vector query, attention is a technique to compute a weighted sum of the vector values, dependent on the vector query. The vector values are the encoder hidden states, and the vector query is the decoder hidden state at the current time step.

The weighted sum can be considered a selective summary of the information present in the vector values. The vector query determines on which of the vector values to focus. Thus, a fixed-size representation of the vector values can be created, in dependence upon the vector query.

The attention scores can be calculated by the dot product, or by weighing the different values (multiplicative attention).

Embeddings

For most machine learning models, the input to the model needs to be numerical. The input to a translation model is a sentence, and words are not numerical. multiple methods exist for the conversion of words into numerical vectors.

These numerical vectors are called the embeddings of the words. Embeddings can be used to convert any type of symbolic representation into a numerical one.

Embeddings can be created by using one-hot encoding. The one-hot vector representing the symbols has the same length as the total number of possible different symbols. Each position in the one-hot vector corresponds to a specific symbol. For example, when converting colors to a numerical vector, the length of the one-hot vector would be the total number of different colors present in the dataset. For each input, the location corresponding to the color of that value is one, whereas all the other locations are valued at zero. This works well for working with images. For NLP, this becomes problematic, because the number of words in a language is very large. This results in enormous models and the need for a lot of computational power. Furthermore, no specific information is captured with one-hot encoding. From the numerical representation, it is not clear that orange and red are more similar than orange and green. For this reason, other methods exist.

A second way of creating embeddings is by creating feature vectors. Every symbol has its specific vector representation, based on features. With colors, a vector of three elements could be used, where the elements represent the amount of yellow, red, and/or blue needed to create the color. Thus, all colors can be represented by only using a vector of three elements. Also, similar colors have similar representation vectors.

For NLP, embeddings based on context, as opposed to words, are small and can be trained. The reasoning behind this concept is that words with similar meanings occur in similar contexts. Different methods take the context of words into account. Some methods, like GloVe, base their context embedding on co-occurrence statistics from corpora (large texts) such as Wikipedia. Words with similar co-occurrence statistics have similar word embeddings. Other methods use neural networks to train the embeddings. For example, they train their embeddings to predict the word based on the context (Common Bag of Words), and/or to predict the context based on the word (Skip-Gram). Training these contextual embeddings is time intensive. For this reason, pre-trained libraries exist. Other deep learning methods can be used to create embeddings. For example, the latent space of a variational autoencoder (VAE) can be used as the embedding of the input. Another method is to use 1D convolutions to create embeddings. This causes a sparse, high-dimensional input space to be converted to a denser, low-dimensional feature space.

Self-Attention: Queries (Q), Keys (K), Values (V)

Transformer models are based on the principle of self-attention. Self-attention allows each element of the input sequence to look at all other elements in the input sequence and search for clues that can help it to create a more meaningful encoding. It is a way to look at which other sequence elements are relevant for the current element. The Transformer can grab context from both before and after the currently processed element.

When performing self-attention, three vectors need to be created for each element of the encoder input: the query vector (Q), the key vector (K), and the value vector (V). These vectors are created by performing matrix multiplications between the input embedding vectors using three unique weight matrices.

After this, self-attention scores are calculated. When calculating self-attention scores for a given element, the dot products between the query vector of this element and the key vectors of all other input elements are calculated. To make the model mathematically more stable, these self-attention scores are divided by the root of the size of the vectors. This has the effect of reducing the importance of the scalar thus emphasizing the importance of the direction of the vector. Just as before, these scores are normalized with a SoftMax layer. This attention distribution is then used to calculate a weighted sum of the value vectors, resulting in a vector z for every input element. In the attention principle explained above, the vector to calculate attention scores and to perform the weighted sum was the same, in self-attention two different vectors are created and used. As the self-attention needs to be calculated for all elements (thus a query for every element), one formula can be created to calculate a Z matrix. The rows of this Z matrix are the z vectors for every sequence input element, giving the matrix a size length sequence dimension QKV.

Figure 14:
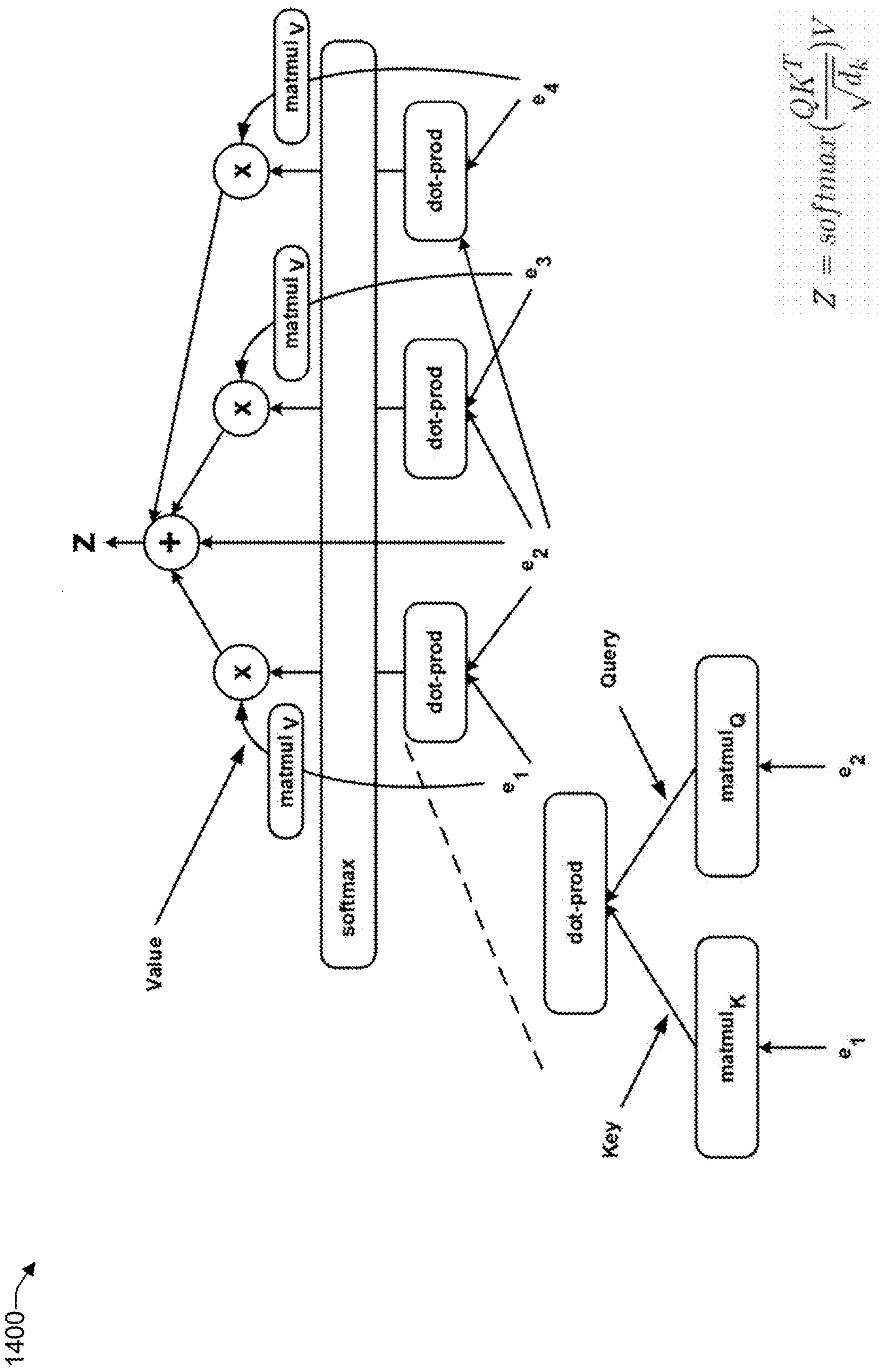
FIG. 14 is a schematic representation of the calculation of self-attention showing one attention head.

Multi-headed attention is executed in the Transformer. FIG. 14 is a schematic representation 1400 of the calculation of self-attention showing one attention head. For every attention head, different weight matrices are trained to calculate Q, K, and V. Every attention head outputs a matrix Z. Different attention heads can capture different types of information. The different Z matrices of the different attention heads are concatenated. This matrix can become large when multiple attention heads are used. To reduce dimensionality, an extra weight matrix W is trained to condense the different attention heads into a matrix with the same size as one Z matrix. This way, the amount of data given to the next step does not enlarge every time self-attention is performed.

When performing self-attention, information about the order of the different elements within the sequence is lost. To address this problem, positional encodings are added to the embedding vectors. Every position has its unique positional encoding vector. These vectors follow a specific pattern, which the Transformer model can learn to recognize. This way, the model can consider distances between the different elements.

As discussed above, in the core of self-attention are three objects: queries (Q), keys (K), and values (V). Each of these objects has an inner semantic meaning of their purpose. One can think of these as analogous to databases. We have a user-defined query of what the user wants to know. Then we have the relations in the database, i.e., the values which are the weights. More advanced database management systems create some apt representation of its relations to retrieve values more efficiently from the relations. This can be achieved by using indexes, which represent information about what is stored in the database. In the context of attention, indexes can be thought of as keys. So instead of running the query against values directly, the query is first executed on the indexes to retrieve where the relevant values or weights are stored. Lastly, these weights are run against the original values to retrieve data that is most relevant to the initial query.

Figure 15:
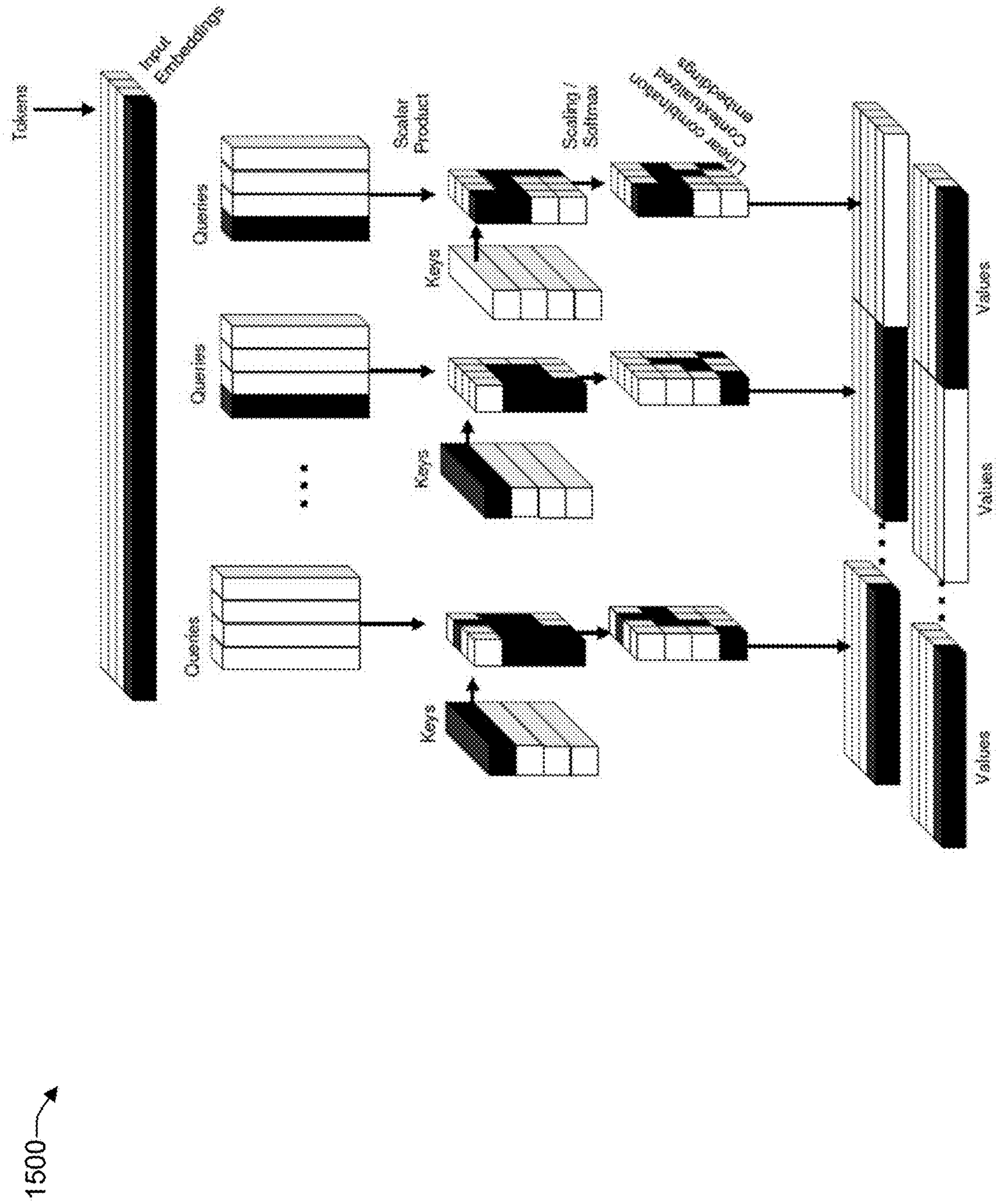
FIG. 15 is a depiction of several attention heads in a Transformer block.

FIG. 15 is a depiction 1500 of several attention heads in a Transformer block. We can see that the outputs of queries and keys dot products in different attention heads are differently colored. This depicts the capability of the multi-head attention to focus on different aspects of the input and aggregate the obtained information by multiplying the input with different attention weights.

Examples of attention calculation include scaled dot-product attention and additive attention. There are several reasons why scaled dot-product attention is used in the Transformers. Firstly, the scaled dot-product attention is relatively fast to compute, since its main parts are matrix operations that can be run on modern hardware accelerators.

Secondly, it performs similarly well for smaller dimensions of the K matrix, dk, as the additive attention. For larger dk, the scaled dot-product attention performs a bit worse because dot products can cause the vanishing gradient problem. This is compensated via the scaling factor, which is defined as $\sqrt{dk}$.

As discussed above, the attention function takes as input three objects: key, value, and query. In the context of Transformers, these objects are matrices of shapes (n, d), where n is the number of elements in the input sequence and dis the hidden representation of each element (also called the hidden vector). Attention is then computed as:

Attention $$(Q, K, V) = \text{SoftMax}\left(\frac{QK^T}{\sqrt{dk}}\right)V,$$

where Q, K, V are computed as:

$$X \cdot W_Q, X \cdot W_K, X \cdot W_V$$

X is the input matrix and $W_Q$, $W_K$, $W_V$ are learned weights to project the input matrix into the representations. The dot products appearing in the attention function are exploited for their geometrical interpretation where higher values of their results mean that the inputs are more similar, i.e., pointing in the geometrical space in the same direction. Since the attention function now works with matrices, the dot product becomes matrix multiplication. The SoftMax function is used to normalize the attention weights into the value of 1 prior to being multiplied by the values matrix. The resulting matrix is used either as input into another layer of attention or becomes the output of the Transformer.

Multi-Head Attention

Transformers become even more powerful when multi-head attention is used. Queries, keys, and values are computed the same way as above, though they are now projected into h different representations of smaller dimensions using a set of h learned weights. Each representation is passed into a different scaled dot-product attention block called a head. The head then computes its output using the same procedure as described above.

Formally, the multi-head attention is defined as:

$$\textit{MultiHeadAttention}\ (Q, K, V) = [\text{head}_1, \ldots, \text{head}_h]W_0 \text{ where head}_i = \text{Attention}\left(QW_i^Q, KW_i^K, VW_i^V\right)$$

The outputs of all heads are concatenated together and projected again using the learned weights matrix $W_0$ to match the dimensions expected by the next block of heads or the output of the Transformer. Using the multi-head attention instead of the simpler scaled dot-product attention enables Transformers to jointly attend to information from different representation subspaces at different positions.

Figure 16:
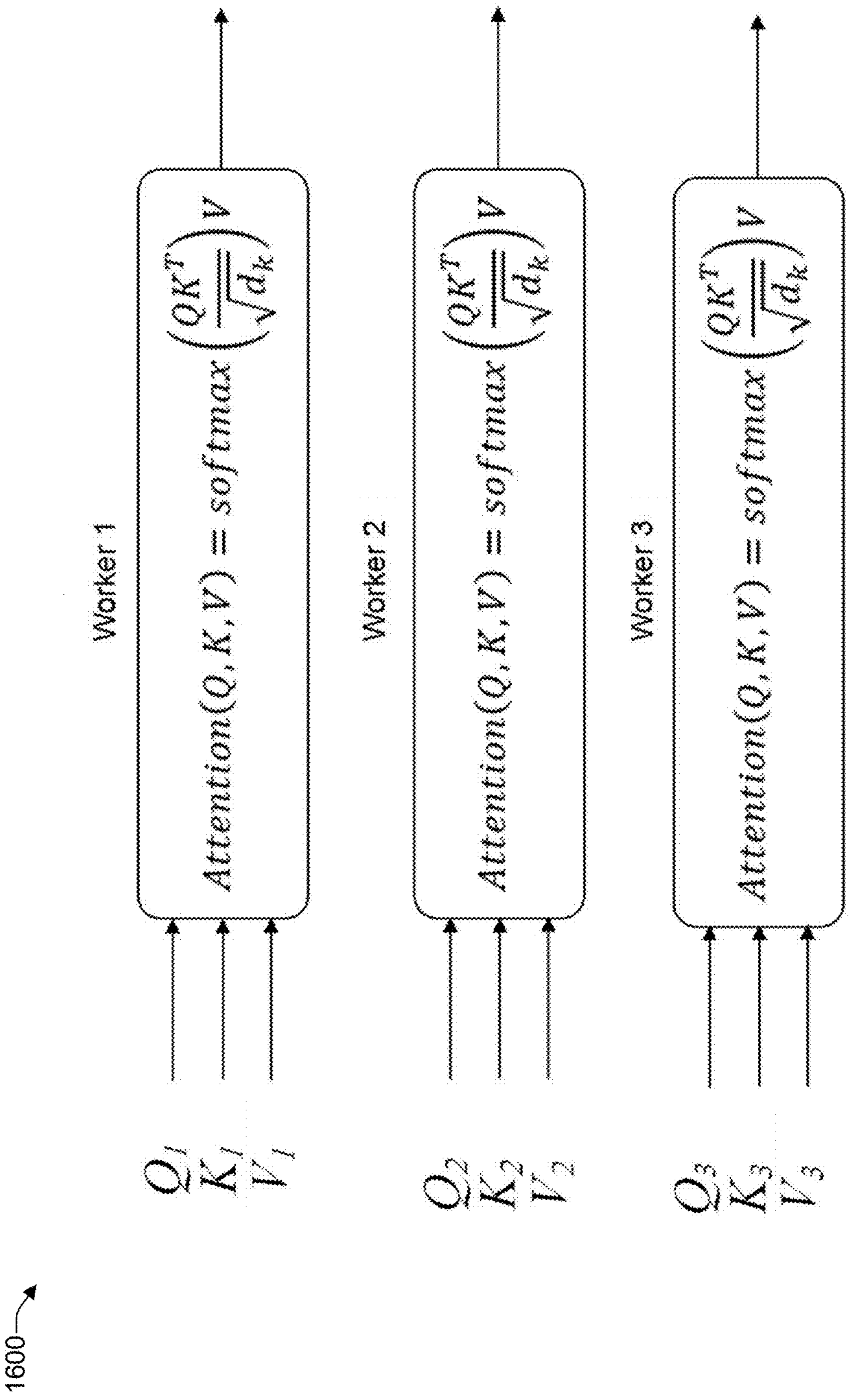
FIG. 16 is an illustration that shows how one can use multiple workers to compute the multi-head attention in parallel, as the respective heads compute their outputs independently of one another.

FIG. 16 is an illustration 1600 that shows how one can use multiple workers to compute the multi-head attention in parallel, as the respective heads compute their outputs independently of one another. Parallel processing is one of the advantages of Transformers over RNNs.

Assuming the naive matrix multiplication algorithm which has a complexity of:

$$a \cdot b \cdot c$$

For matrices of shape (a, b) and (c, d), to obtain values Q, K, V, we need to compute the operations:

$$X \cdot W_Q, X \cdot W_K, X \cdot W_V$$

The matrix X is of shape (n, d) where n is the number of patches and d is the hidden vector dimension. The weights $W_Q$, $W_K$, $W_V$ are all of shape (d, d). Omitting the constant factor 3, the resulting complexity is:

$$n \cdot d^2$$

We can proceed to the estimation of the complexity of the attention function itself, i.e., of SoftMax $$\left(\frac{QK^T}{\sqrt{dk}}\right)V.$$

The matrices Q and K are both of shape (n, d). The transposition operation does not influence the asymptotic complexity of computing the dot product of matrices of shapes (n, d)·(d, n), therefore its complexity is:

$$n^2 \cdot d$$

Scaling by a constant factor of $\sqrt{dk}$, where dk is the dimension of the keys vector, as well as applying the SoftMax function, both have the complexity of a·b for a matrix of shape (a, b), hence they do not influence the asymptotic complexity. Lastly the dot product SoftMax $$\left(\frac{QK^T}{\sqrt{dk}}\right) \cdot V$$

is between matrices of shapes (n, n) and (n, d) and so its complexity is:

$$n^2 \cdot d$$

The final asymptotic complexity of scaled dot-product attention is obtained by summing the complexities of computing Q, K, V, and of the following attention function:

$$n \cdot d^2 + n^2 \cdot d$$

The asymptotic complexity of multi-head attention is the same since the original input matrix X is projected into h matrices of shapes $$\left(n, \frac{d}{h}\right),$$

where h is the number of heads. From the point of view of asymptotic complexity, h is constant, therefore we would arrive at the same estimate of asymptotic complexity using a similar approach as for the scaled dot-product attention.

Transformer models often have the encoder-decoder architecture, although this is not necessarily the case. The encoder is built out of different encoder layers which are all constructed in the same way. The positional encodings are added to the embedding vectors. Afterward, self-attention is performed.

Encoder Block of Transformer

Figure 17:
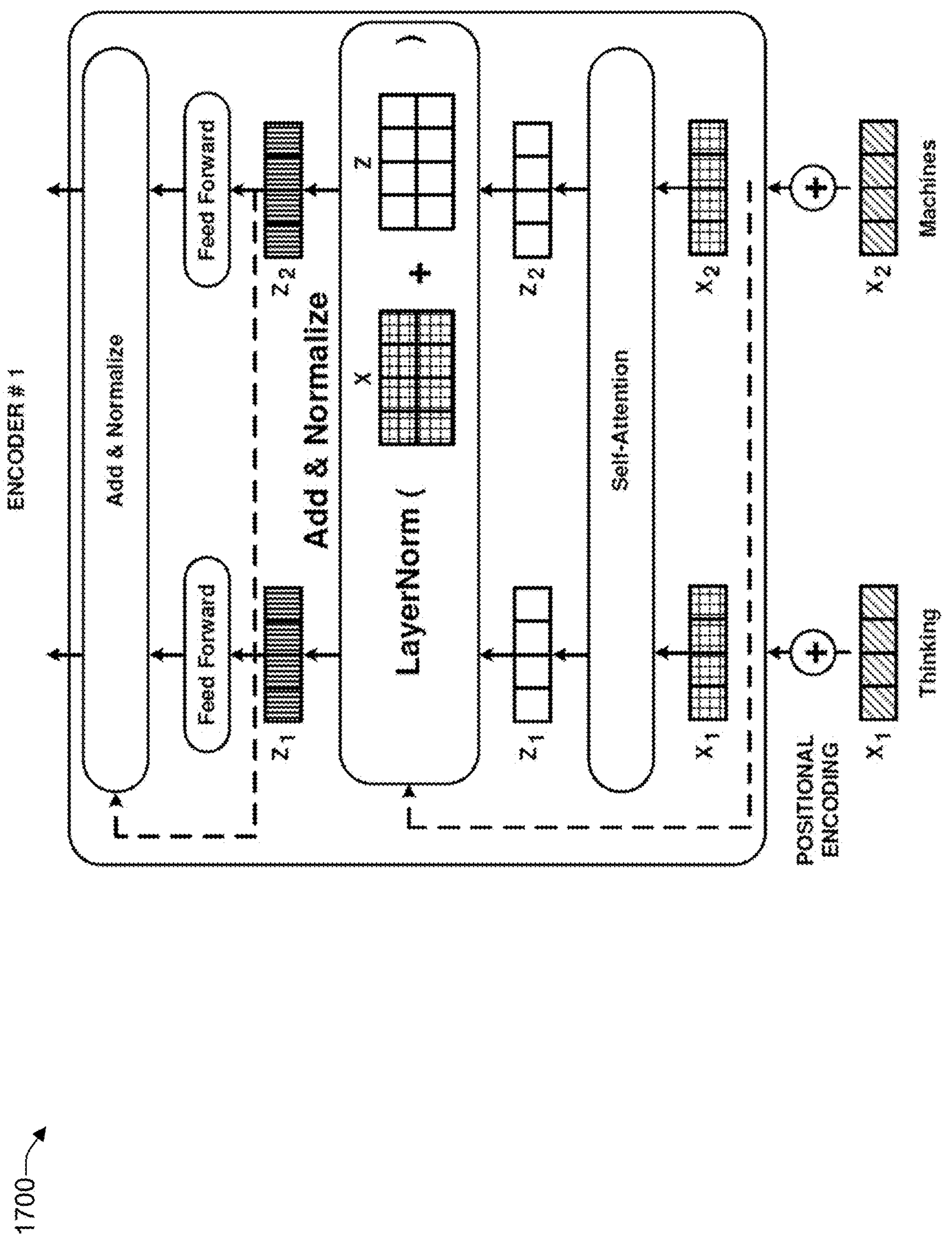
FIG. 17 is a portrayal of one encoder layer of a Transformer network.

FIG. 17 is a portrayal 1700 of one encoder layer of a Transformer network. Every self-attention layer is surrounded by a residual connection, summing up the output and input of the self-attention. This sum is normalized, and the normalized vectors are fed to a feed-forward layer. Every z vector is fed separately to this feed-forward layer. The feed-forward layer is wrapped in a residual connection and the outcome is normalized too. Often, numerous encoder layers are piled to form the encoder. The output of the encoder is a fixed-size vector for every element of the input sequence.

Just like the encoder, the decoder is built from different decoder layers. In the decoder, a modified version of self-attention takes place. The query vector is only compared to the keys of previous output sequence elements. The elements further in the sequence are not known yet, as they still must be predicted. No information about these output elements may be used.

Encoder-Decoder Blocks of Transformer

Figure 18:
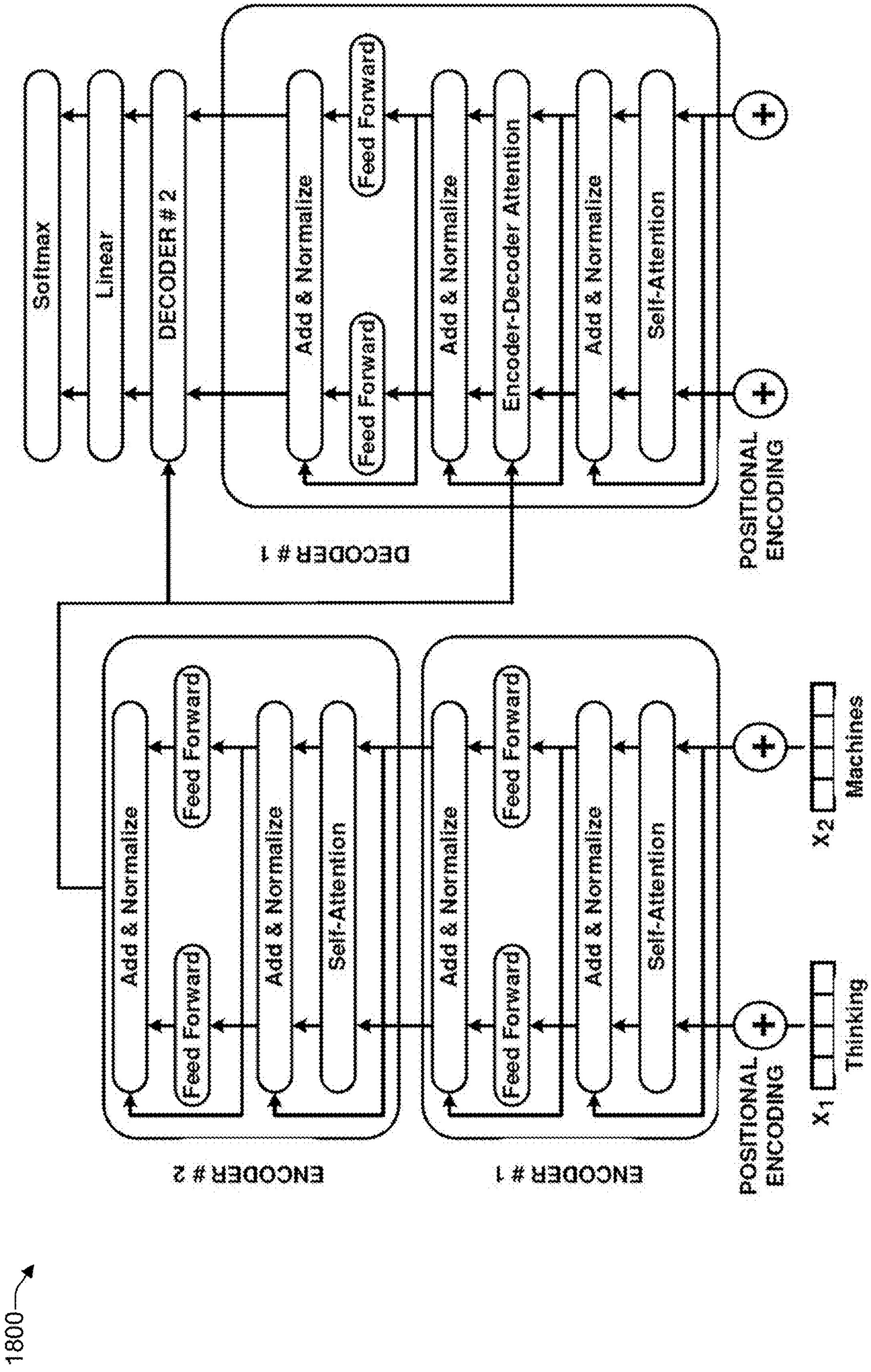
FIG. 18 shows a schematic overview of a Transformer model.

FIG. 18 shows a schematic overview 1800 of a Transformer model. Next to a self-attention layer, a layer of encoder-decoder attention is present in the decoder, in which the decoder can examine the last Z vectors of the encoder, providing fluent information transmission. The ultimate decoder layer is a feed-forward layer. All layers are packed in a residual connection. This allows the decoder to examine all previously predicted outputs and all encoded input vectors to predict the next output. Thus, information from the encoder is provided to the decoder, which could improve the predictive capacity. The output vectors of the last decoder layer need to be processed to form the output of the entire system. This is done by a combination of a feed-forward layer and a SoftMax function. The output corresponding to the highest probability is the predicted output value for a subject time step.

For some tasks other than translation, only an encoder is needed. This is true for both document classification and name entity recognition. In these cases, the encoded input vectors are the input of the feed-forward layer and the SoftMax layer. Transformer models have been extensively applied in different NLP fields, such as translation, document summarization, speech recognition, and named entity recognition. These models have applications in the field of biology as well for predicting protein structure and function and labeling DNA sequences.

Vision Transformer

There are extensive applications of transformers in vision including popular recognition tasks (e.g., image classification, object detection, action recognition, and segmentation), generative modeling, multi-modal tasks (e.g., visual-question answering, visual reasoning, and visual grounding), video processing (e.g., activity recognition, video forecasting), low-level vision (e.g., image super-resolution, image enhancement, and colorization) and 3D analysis (e.g., point cloud classification and segmentation).

Figure 19:
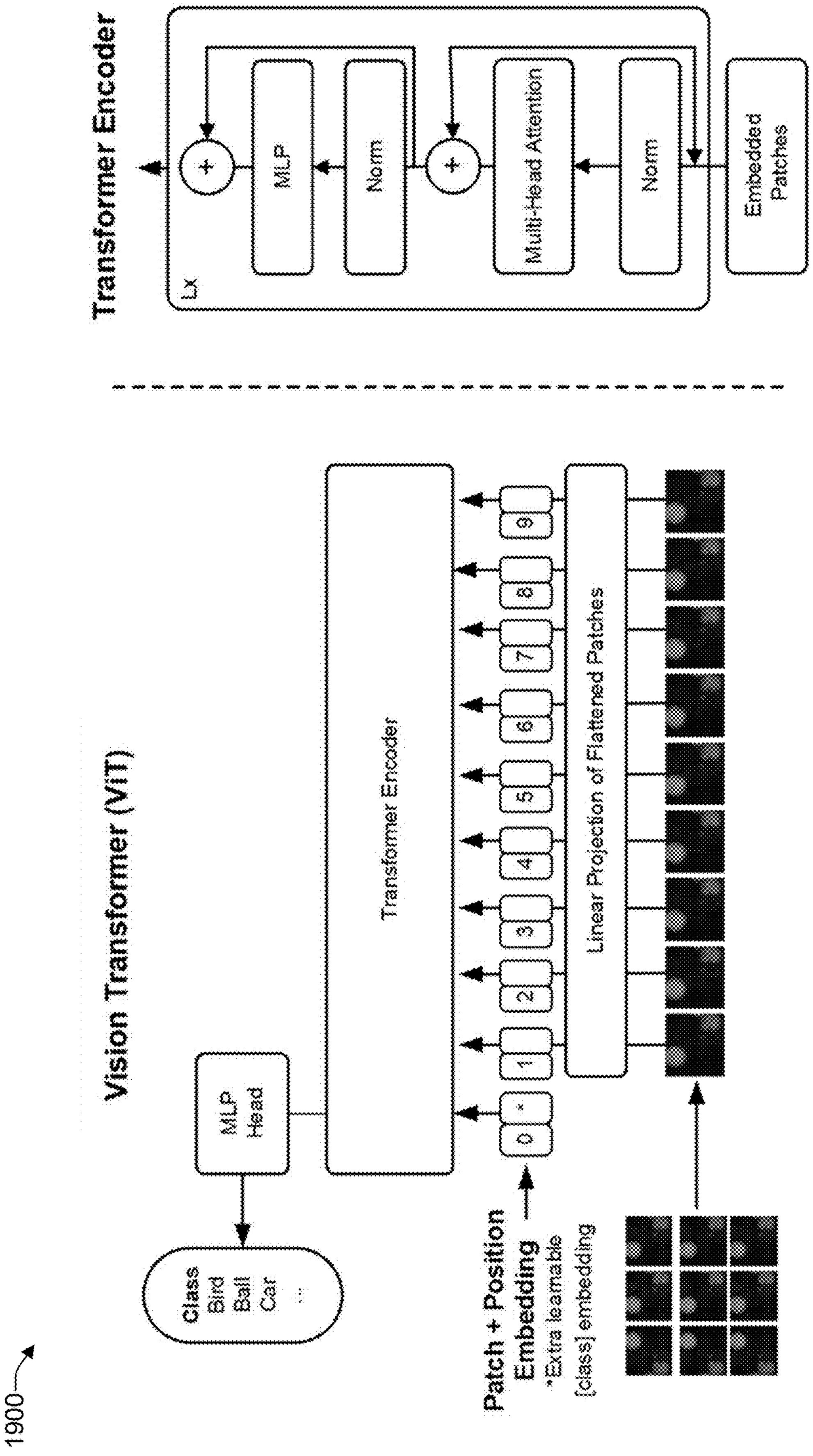
FIG. 19 is a depiction of a Vision Transformer (ViT).
Figure 20:
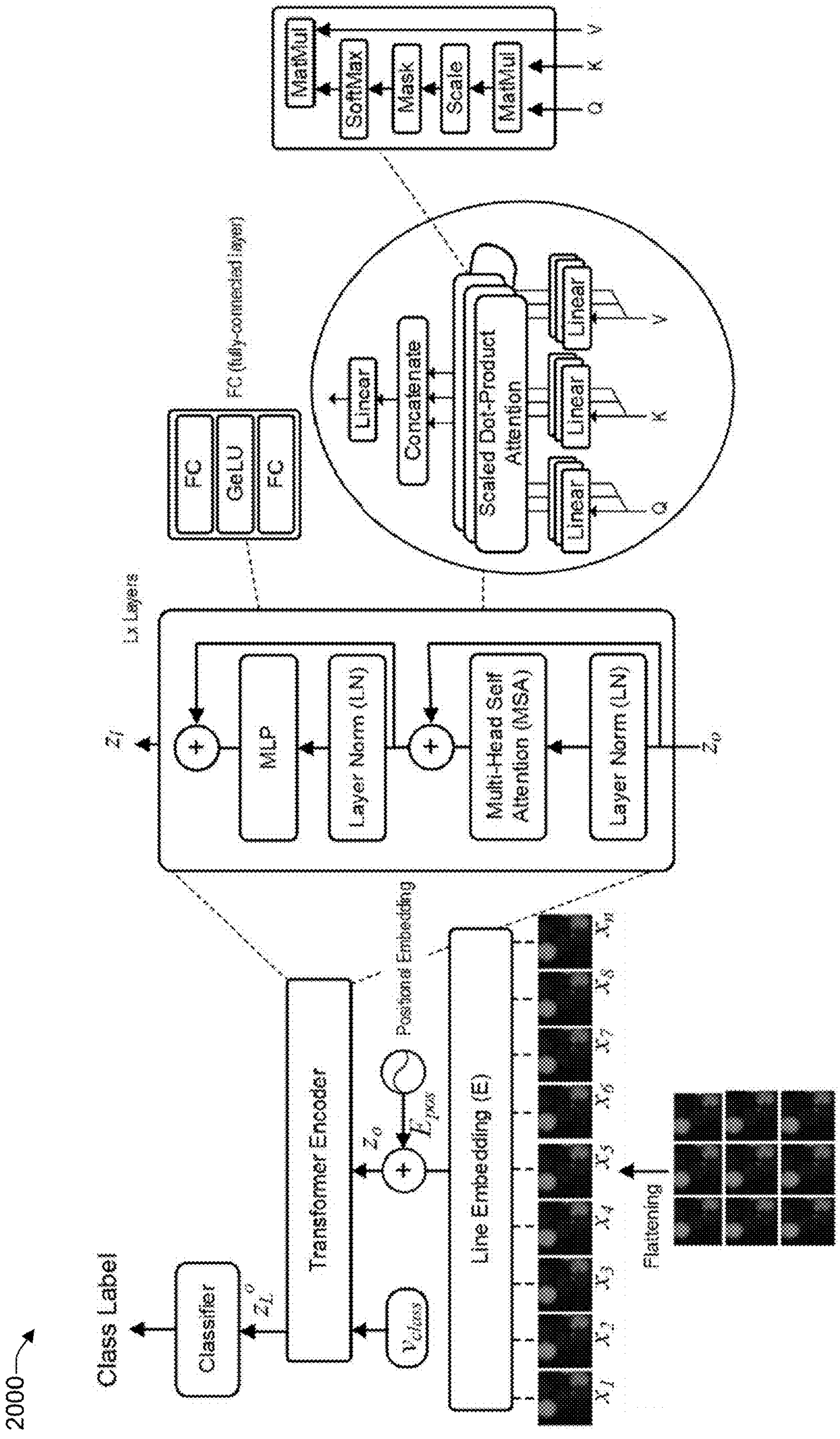
FIG. 20 illustrates a processing flow of the Vision Transformer (ViT).

FIG. 19 is a depiction 1900 of a Vision Transformer (ViT). FIG. 20 illustrates a processing flow 2000 of the Vision Transformer (ViT). Transformers were originally developed for NLP and worked with sequences of words. In image classification, we often have a single input image in which the pixels are in a sequence. To reduce the computation required, Vision Transformers (ViTs) cut the input image into a set of fixed-sized patches of pixels. The patches are often 16×16 pixels. They are treated much like words in NLP Transformers. ViTs are depicted in FIGS. 19 and 20. Unfortunately, important positional information is lost because image sets are position-invariant. This problem is solved by adding a learned positional encoding into the image patches.

The computations of the ViT architecture can be summarized as follows. The first layer of a ViT extracts a fixed number of patches from an input image (FIG. 19). The patches are then projected to linear embeddings. A special class token vector is added to the sequence of embedding vectors to include all representative information of all tokens through the multi-layer encoding procedure. The class vector is unique to each image. Vectors containing positional information are combined with the embeddings and the class token. The sequence of embedding vectors is passed into the Transformer blocks. The class token vector is extracted from the output of the last Transformer block and is passed into a multilayer perceptron (MLP) head whose output is the final classification. The perceptron takes the normalized input and places the output in categories. It classifies the images. FIG. 21 shows example software code 2100 that implements a Transformer block. This procedure directly translates into the Python Keras code shown in FIG. 21.

When the input image is split into patches, a fixed patch size is specified before instantiating a ViT. Given the quadratic complexity of attention, patch size has a large effect on the length of training and inference time. A single Transformer block comprises several layers. The first layer implements Layer Normalization, followed by the multi-head attention that is responsible for the performance of ViTs. In the depiction of a Transformer block in FIG. 19, we can see two arrows. These are residual skip connections. Including skip connection data can simplify the output and improve the results. The output of the multi-head attention is followed again by Layer Normalization. And finally, the output layer is an MLP (Multi-Layer Perceptron) with the GELU (Gaussian Error Linear Unit) activation function.

ViTs can be pretrained and fine-tuned. Pretraining is generally done on a large dataset. Fine-tuning is done on a domain specific dataset.

Domain-specific architectures, like convolutional neural networks (CNNs) or long short-term memory networks (LSTMs), have been derived from the usual architecture of MLPs and suffer from so-called inductive biases that predispose the networks towards a certain output. ViTs stepped in the opposite direction of CNNs and LSTMs and became more general architectures by eliminating inductive biases. A ViT can be seen as a generalization of MLPs because MLPs, after being trained, do not change their weights for different inputs. On the other hand, ViTs compute their attention weights at runtime based on the particular input.

What is claimed is:

1. A conversational artificial intelligence system, comprising:

a plurality of large language models, wherein individual large language models in the plurality are configured to perform different functions;

a routing system configured to route a request to a large language model, selected from the plurality of large language models, that is best suited for a task associated with the request;

a conversation manager configured to coordinate a flow of a conversation between the system and a user using the plurality of large language models;

a supervisory module configured to operate in parallel with the conversation and audit responses generated during the conversation, the supervisory module providing feedback that contributes to construction of downstream responses to the user; and one or more safety modules configured to prevent the system from performing actions that are outside of defined constraints.

2. The conversational artificial intelligence system of claim 1, wherein the routing system is configured to route the request based on at least one of a latency requirement, a domain of the request, or a classification task.

3. The conversational artificial intelligence system of claim 1, wherein the conversation manager is configured to orchestrate the plurality of large language models to process speech, interpret meaning, and generate responses in parallel.

4. The conversational artificial intelligence system of claim 1, wherein the different functions include at least two of: intake, scheduling, order processing, pre-operative preparation, discharge, or navigation.

5. The conversational artificial intelligence system of claim 1, wherein the supervisory module is implemented using a large language model that is different from a large language model used by the conversation manager to generate the responses.

6. The conversational artificial intelligence system of claim 1, wherein the system comprises a plurality of supervisory modules, individual supervisory modules configured to perform different supervisory functions.

7. The conversational artificial intelligence system of claim 1, wherein the supervisory module is configured to determine whether a response is to be clarified and, in response to a determination that the response is to be clarified, provide feedback to the conversation manager causing the conversation manager to provide a clarification to the user during the conversation.

8. The conversational artificial intelligence system of claim 1, wherein the one or more safety modules are configured to detect and intercept threat vectors.

9. The conversational artificial intelligence system of claim 1, further comprising redundancy across model providers, wherein the routing system is configured to fail over to a different large language model when a first large language model degrades.

10. The conversational artificial intelligence system of claim 1, wherein the conversation is an audio-based conversation, and the system further comprises an automatic speech recognition module and a text-to-speech module.

11. The conversational artificial intelligence system of claim 1, wherein the supervisory module is further configured to transfer the conversation to a human when the supervisory module determines that a clarification is insufficient.

12. The conversational artificial intelligence system of claim 1, wherein the routing system routes the request to a large language model that is fine-tuned for a specific domain.

13. The conversational artificial intelligence system of claim 1, wherein the conversation manager coordinates the flow of the conversation across a plurality of channels including at least two of: voice, chat, email, or messaging.

14. A computer-implemented method for operating a conversational artificial intelligence system that includes a plurality of large language models, the method comprising:

configuring individual large language models in the plurality to perform different functions;

routing, by a routing system, a request to a large language model, selected from the plurality of large language models, that is best suited for a task associated with the request;

coordinating, by a conversation manager, a flow of a conversation between the system and a user using the plurality of large language models;

auditing, by a supervisory module operating in parallel with the conversation, responses generated during the conversation, and providing feedback that contributes to construction of downstream responses to the user; and preventing, by one or more safety modules, the system from performing actions that are outside of defined constraints.

15. The method of claim 14, wherein the routing comprises routing the request based on at least one of a latency requirement, a domain of the request, or a classification task.

16. The method of claim 14, further comprising orchestrating the plurality of large language models to process speech, interpret meaning, and generate responses in parallel.

17. The method of claim 14, wherein the auditing comprises determining whether a response is to be clarified and, in response to a determination that the response is to be clarified, providing feedback causing the conversation manager to provide a clarification to the user during the conversation.

18. The method of claim 14, further comprising failing over, by the routing system, to a different large language model when a first large language model degrades.

19. A non-transitory computer-readable medium storing instructions that, when executed by one or more processors, cause the one or more processors to:

route, by a routing system, a request to a large language model, selected from a plurality of large language models configured to perform different functions, that is best suited for a task associated with the request;

coordinate, by a conversation manager, a flow of a conversation between a conversational artificial intelligence system and a user using the plurality of large language models;

audit, by a supervisory module operating in parallel with the conversation, responses generated during the conversation, and provide feedback that contributes to construction of downstream responses to the user; and prevent, by one or more safety modules, the system from performing actions that are outside of defined constraints.

20. The non-transitory computer-readable medium of claim 19, wherein the plurality of large language models includes at least one commercial large language model and at least one proprietary large language model.

* * * * *